US012564367B2

(12) United States Patent
Fouras et al.

(10) Patent No.: US 12,564,367 B2

(45) Date of Patent: Mar. 3, 2026

(54) IMAGING DEVICE AND METHOD FOR MULTIPLE IMAGE ACQUISITION

(71) Applicant: AUSTRALIAN LUNG HEALTH INITIATIVE PTY LTD, Carlton (AU)

(72) Inventors: Andreas Fouras, Carlton (AU); Paul Chapman, Carlton (AU)

(73) Assignee: AUSTRALIAN LUNG HEALTH INITIATIVE PTY LTD, Carlton (AU)

( * ) Notice: Subject to any disclaimer, the term of this patent is extended or adjusted under 35 U.S.C. 154(b) by 367 days.

(21) Appl. No.: 18/003,143

(22) PCT Filed: Jun. 25, 2021

(86) PCT No.: PCT/AU2021/050669
§ 371 (c)(1),
(2) Date: Dec. 22, 2022

(87) PCT Pub. No.: WO2021/258156
PCT Pub. Date: Dec. 30, 2021

(65) Prior Publication Data
US 2023/0346328 A1 Nov. 2, 2023

Related U.S. Application Data

(60) Provisional application No. 63/044,090, filed on Jun. 25, 2020, provisional application No. 63/043,994, filed on Jun. 25, 2020.

(51) Int. Cl.
*A61B 6/40* (2024.01)
*A61B 5/055* (2006.01)
(Continued)

(52) U.S. Cl.
CPC .............. *A61B 6/541* (2013.01); *A61B 5/055* (2013.01); *A61B 6/032* (2013.01); *A61B 6/463* (2013.01);
(Continued)

(58) Field of Classification Search
CPC ......... A61B 6/541; A61B 5/055; A61B 6/032; A61B 6/463; A61B 6/486; A61B 5/113;
(Continued)

(56) References Cited

U.S. PATENT DOCUMENTS

| | | | |
|---|---|---|---|
| 7,231,076 B2 * | 6/2007 | Fu | ............................ G06T 7/238 |
| | | | 382/294 |
| 8,457,717 B2 | 6/2013 | Keall et al. | |

(Continued)

FOREIGN PATENT DOCUMENTS

| | | |
|---|---|---|
| CN | 108013885 A | 5/2018 |
| JP | 2017-511239 A | 4/2017 |

(Continued)

OTHER PUBLICATIONS

Extended European Search Report dated Feb. 1, 2024 from corresponding European Patent Application No. 21827841.4, 5 pages.

(Continued)

*Primary Examiner* — Siamak Harandi

(74) *Attorney, Agent, or Firm* — Ruggiero McAllister & McMahon LLC

(57) ABSTRACT

An imaging device for acquiring a time series of in vivo images of a subject's body is provided. The imaging device includes energy sources, detectors for detecting energy from the energy sources passing through the subject's body located between the energy sources and detectors, and a controller configured to operate the energy sources and detectors to acquire a time series of in vivo images of the subject's body. Pairs of energy sources and detectors are spatially positioned around the subject's body in a first plane, and a pair of energy sources and detectors is spatially positioned around the subject's body in a second plane. The first plane and the second plane intersect through the subject's body to be imaged. A method for acquiring a time (Continued)

series of in vivo images of a subject's body using the imaging device is also provided.

24 Claims, 14 Drawing Sheets

(51) Int. Cl.

| | |
|---|---|
| *A61B 6/00* | (2006.01) |
| *A61B 6/03* | (2006.01) |
| *A61B 6/46* | (2024.01) |
| *G06T 7/00* | (2017.01) |
| *A61B 5/113* | (2006.01) |

(52) U.S. Cl.
CPC ............ *A61B 6/486* (2013.01); *G06T 7/0012* (2013.01); *A61B 5/113* (2013.01); *G06T 2207/30061* (2013.01)

(58) Field of Classification Search
CPC .......... A61B 5/6888; A61B 2562/0261; A61B 5/0077; A61B 5/0816; A61B 5/7292; A61B 6/4014; A61B 6/487; A61B 6/5205; A61B 6/0442; A61B 6/0478; A61B 6/08; A61B 8/40; A61B 8/4416; A61B 8/543; A61B 5/004; A61B 5/087; A61B 5/0878; A61B 6/527; A61B 8/5276; A61B 6/022; A61B 8/5253; A61B 5/1128; A61B 5/706; A61B 6/5217; G06T 7/0012; G06T 2207/30061; G06T 7/20; G06T 2207/10116; G01N 23/04
See application file for complete search history.

(56) References Cited

U.S. PATENT DOCUMENTS

| | | | | |
|---|---|---|---|---|
| 9,025,849 | B2 | 5/2015 | Fouras et al. | |
| 9,538,976 | B2 | 1/2017 | Keall et al. | |
| 2011/0058651 | A1 * | 3/2011 | Fuerst | G01N 23/046 |
| | | | | 378/58 |
| 2014/0177785 | A1 | 6/2014 | Funk | |
| 2015/0282774 | A1 | 10/2015 | Lee et al. | |
| 2017/0143289 | A1 | 5/2017 | Fouras | |
| 2019/0126070 | A1 | 5/2019 | Hsieh | |

FOREIGN PATENT DOCUMENTS

| | | | | |
|---|---|---|---|---|
| JP | 2020-065840 | A | 4/2020 | |
| WO | WO-2009115982 | A1 * | 9/2009 | ............. A61B 6/027 |
| WO | 2011/032210 | A1 | 3/2011 | |
| WO | 2015/157799 | A1 | 10/2015 | |

OTHER PUBLICATIONS

International Preliminary Examination Report dated Jan. 5, 2023 from corresponding International Patent Application No. PCT/AU2021/050669, 8 pages.
International Search Report dated Sep. 13, 2021 from corresponding International Patent Application No. PCT/AU2021/050669, 4 pages.
Written Opinion dated Sep. 13, 2021 from corresponding International Patent Application No. PCT/AU2021/050669, 6 pages.
Kim et al.; "Dual source and dual detector arrays tetrahedron beam computed tomography for image guided radiotherapy", Phys. Med. Biol. 59, 2014, pp. 615-630.

* cited by examiner

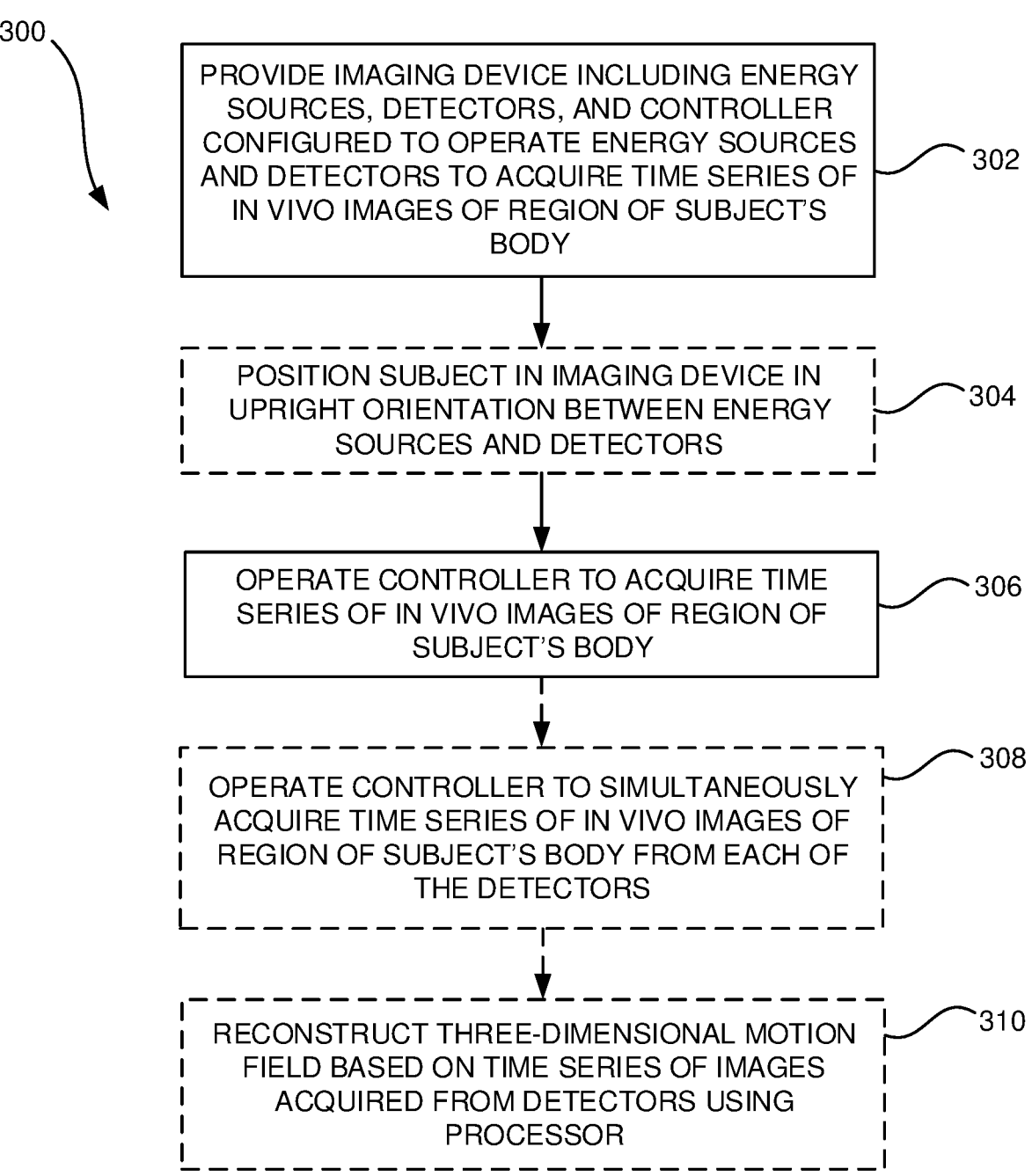

300

PROVIDE IMAGING DEVICE INCLUDING ENERGY SOURCES, DETECTORS, AND CONTROLLER CONFIGURED TO OPERATE ENERGY SOURCES AND DETECTORS TO ACQUIRE TIME SERIES OF IN VIVO IMAGES OF REGION OF SUBJECT'S BODY — 302

POSITION SUBJECT IN IMAGING DEVICE IN UPRIGHT ORIENTATION BETWEEN ENERGY SOURCES AND DETECTORS — 304

OPERATE CONTROLLER TO ACQUIRE TIME SERIES OF IN VIVO IMAGES OF REGION OF SUBJECT'S BODY — 306

OPERATE CONTROLLER TO SIMULTANEOUSLY ACQUIRE TIME SERIES OF IN VIVO IMAGES OF REGION OF SUBJECT'S BODY FROM EACH OF THE DETECTORS — 308

RECONSTRUCT THREE-DIMENSIONAL MOTION FIELD BASED ON TIME SERIES OF IMAGES ACQUIRED FROM DETECTORS USING PROCESSOR — 310

Figure 14

IMAGING DEVICE AND METHOD FOR MULTIPLE IMAGE ACQUISITION

CROSS REFERENCE TO RELATED APPLICATIONS

This application is a national stage entry of International Application No. PCT/AU2021/050669 filed on Jun. 25, 2021, which claims priority from U.S. Provisional Patent Application No. 63/043,994 filed on 25 Jun. 2020, and from U.S. Provisional Patent Application No. 63/044,090 filed on 25 Jun. 2020, the contents of each of which are incorporated by reference herein in its entirety.

TECHNICAL FIELD

The present disclosure relates to an imaging device and method for acquiring a time series of in vivo images of a region of a human or animal subject's body, and for acquiring multiple images from different perspectives. It also relates particularly but not exclusively to dynamic in vivo imaging of an organ, such as the lungs or heart of the subject.

BACKGROUND

Current imaging modalities such as X-ray, Computed Tomography (CT) imaging and Magnetic Resonance Imaging (MRI) provide methods to examine the structure and function of organs of a patient, such as the lungs, heart and brain. However, structural lung change often arises after disease establishment, eliminating the possibility of disease-prevention treatments (e.g., in early cystic fibrosis). While high-resolution CT imaging can provide excellent structural detail, it is costly and the relatively high levels of radiation exposure (a high-resolution CT is often equivalent to 70 chest X-rays) are of concern. Due to ionizing radiation dose, use of X-ray based techniques (especially CT) for detection and treatment of various diseases, including acute respiratory disease, is severely restricted for vulnerable patients, such as infants and children who are more susceptible to tissue damage due to radiation. Furthermore, the inherent measurement limitations also severely restrict evidence-based detection and treatment of acute respiratory disease across all ages of patients.

XV technology developed by 4DMedical has offered a breakthrough in clinical lung function assessment. The XV technology is disclosed in patent applications published as WO 2011/032210 A1 and WO 2015/157799 A1. The current XV technique uniquely combines X-ray imaging with proprietary flow velocimetry algorithms to measure motion in all locations of the lung in fine spatial and temporal detail, enabling regional lung function measurements throughout the respiratory cycle, at every location within the lung. This approach enables detection of even subtle functional losses well before lung structure is irreversibly affected by disease, meaning that treatment may be applied early, when it has the greatest impact and the best chance of success.

Current XV technology is used in clinical applications via a Software as a Service (SaaS) model, whereby scans of the patient's lungs are acquired using existing fluoroscopic X-ray equipment. The scans are then processed using software algorithms, via a cloud-based server, to provide functional imaging analysis of the patient's lungs over time. However, the accuracy and quality of the XV analysis is limited by the images able to be acquired using existing medical scanners which require patients to remain still and breathe in a controlled fashion during scanning. This restricts access to many patient groups, including young children, the elderly, and patients with language, hearing or cognitive impairment, who are unable to be readily scanned due to positioning issues within the scanner and/or the inability to follow instructions for the scanning to be completed.

Computed Tomography (CT) scanners are commonly used to acquire cross-sectional images of a subject's body. Typical CT scanner arrangements employ a ring or c-shaped arm on which one energy source and typically one detector or detector array are mounted for rotation around the subject's body. Multiple images are acquired through X-ray measurements taken from different angles as the ring or c-shaped arm rotates which are used to produce cross-sectional images of the subject's body. A disadvantage of existing medical scanners, such as CT scanners, is that a large scanner is typically required for rotation around the subject's body to acquire images at different angles. It would be desirable to provide a smaller, more compact imaging device that allows multiple images to be acquired at different angles without the need for moving parts during acquisition.

Furthermore, existing medical scanners, such as CT scanners, often employ X-rays which result in a high burden of X-ray radiation for the subject when multiple images are acquired at different angles for in vivo imaging. It would be desirable to reduce the X-ray dosage by shortening the operating time of the energy source and detector or detector array to acquire the images. Reducing the x-ray dosage is particularly beneficial to vulnerable patient groups, such as infants and children, who are more susceptible to tissue damage due to radiation.

FIGS. 1 and 2 illustrate an example of a system 10 for imaging a region 230 of a subject's body 210. System 10 includes three energy sources 11 and three detectors 12 spatially positioned in a common plane and located on a common arc 14 around the subject's body 210. The energy sources 11 and detectors 12 are stationary during scanning, adopting a fixed position in the system 10, in contrast to CT scanners with the rotating ring or c-shaped arm. The subject 200 may be positioned on a tray or bed 18 during imaging as shown. The spatial arrangement of the energy sources 11 and detectors 12 enables three imaging angles through the region 230 of the subject's body 210 to be captured during imaging as indicated by the imaging beams 16. FIG. 2 is a plan view of the system 10 of FIG. 1 omitting the detectors 12 for clarity and showing that the common plane with common arc 14 may be a transverse plane through the subject's body 210.

While the system 10 can capture multiple imaging angles, it requires the energy sources 11 and detectors 12 to be sufficiently spaced around the subject's body 210 in order to obtain enough imaging data for optimising image acquisition, such as for providing dynamic in vivo imaging capability. The energy sources 11 and detectors 12 of the system 10 shown in FIGS. 1 and 2 are equally spaced circumferentially around the subject's body 210 across a 360 degree angle. Similar to CT scanners, this arrangement would necessitate providing a large scanning device to acquire images at different angles where the stationary energy sources and detectors surround the patient's body.

Another disadvantage of existing medical scanners, such as CT scanners and the system 10 of FIGS. 1 and 2, is that the patient is often positioned in a patient tray or bed 18 in the scanner in a supine position. For dynamic imaging of the subject's lungs, the patient is required to remain still and breathe in a controlled fashion during scanning. This restricts access of the imaging technology to many patient groups, including young children, the elderly, and patients with language, hearing or cognitive impairment, who are unable to be readily scanned due to positioning issues within the scanners and/or the inability to follow instructions for the scanning to be completed.

Therefore, it would be desirable to provide an imaging device and method of imaging that acquires in vivo images of a patient's body, ideally suitable for analysis with the XV technology, with multiple images being acquired from different perspectives, and which may reduce the size of the imaging device and enable access to many patient groups. It would also be desirable to provide an imaging device and method of imaging which ameliorates and/or overcomes one or more problems or inconveniences of the prior art.

A reference herein to a patent document or any other matter identified as prior art, is not to be taken as an admission that the document or other matter was known or that the information it contains was part of the common general knowledge as at the priority date of any of the claims.

SUMMARY

In one aspect, the present disclosure provides an imaging device for acquiring a time series of in vivo images of a region of a subject's body. The imaging device includes at least three energy sources, at least three detectors for detecting energy from the at least three energy sources passing through the region of the subject's body located between the energy sources and detectors, and a controller configured to operate the energy sources and detectors to acquire a time series of in vivo images of the region of the subject's body. At least two pairs of energy sources and detectors are spatially positioned around the subject's body in a first plane, and at least one pair of energy sources and detectors is spatially positioned around the subject's body in a second plane. The first plane and the second plane intersect through the region of the subject's body to be imaged.

The controller may be configured to acquire the images using at least three imaging angles through the region of the subject's body. At least two imaging angles may be provided in the first plane through the subject's body, and at least one imaging angle may be provided in the second plane through the subject's body.

In some embodiments, the at least two imaging angles are spaced apart in a range of about 45 to 90 degrees. Preferably, the at least two imaging angles are spaced apart in a range of about 45 to 70 degrees or about 70 to 90 degrees, or about 45 to 60 degrees, about 60 to 70 degrees, about 70 to 80 degrees or about 80 to 90 degrees. The spacing may be about 45 degrees, about 50 degrees, about 55 degrees, about 60 degrees, about 65 degrees, about 70 degrees, about 75 degrees, about 80 degrees, about 85 degrees or about 90 degrees. Preferably, the spacing is about 80 degrees. However, in other embodiments, the spacing may be preferably about 60 degrees, depending on the spatial positioning of the at least two pairs of energy sources and detectors in the first plane.

In some embodiments, at least one of the detectors is angled relative to the respective energy source. The at least one detector may indirectly face the respective energy source. The at least one detector may be angled such that the imaging beam generated by the energy source is not substantially orthogonal with the detector. In some embodiments, at least one of the detectors is substantially aligned with the respective energy source. The at least one detector may directly face the respective energy source. The at least one detector may be substantially aligned such that the imaging beam generated by the energy source is substantially orthogonal to the detector. In some embodiments, the imaging device includes at least one detector angled relative to the respective energy source and at least one detector substantially aligned with the respective energy source. Preferably, at least two of the detectors or all of the detectors are angled relative to the respective energy sources in order to provide a smaller, more compact imaging device that still allows for multiple images to be acquired at different angles through the subject's body.

The at least two energy sources and the at least two detectors in the first plane may be each located on a respective common arc in the first plane. In some embodiments, the two energy sources and two detectors are located on the same common arc in the first plane. In embodiments where the two energy sources and two detectors are located on different common arcs, the length of the common arc on which the energy sources are located preferably has a greater length than the common arc on which the detectors are located.

The at least three energy sources and the at least three detectors may be each spaced apart in one of an approximately triangular-shaped or L-shaped configuration.

In some embodiments, the imaging device further includes at least four energy sources and at least four detectors. At least three pairs of energy sources and detectors may be spatially positioned in the first plane, and at least one pair of energy sources and detectors may be spatially positioned in the second plane.

The controller may be configured to acquire the images using at least four imaging angles through the region of the subject's body. At least three imaging angles may be provided in the first plane through the subject's body, and at least one imaging angle may be provided in the second plane through the subject's body.

In some embodiments, the at least three imaging angles in the first plane may be spaced apart from each other in a range of about 45 to 90 degrees. Preferably, the at least three imaging angles are spaced apart from each other in a range of about 45 to 70 degrees or about 70 to 90 degrees, or about 45 to 60 degrees, about 60 to 70 degrees, about 70 to 80 degrees or about 80 to 90 degrees. The spacing may be about 45 degrees, about 50 degrees, about 55 degrees, about 60 degrees, about 65 degrees, about 70 degrees, about 75 degrees, about 80 degrees, about 85 degrees or about 90 degrees. Preferably, the spacing is about 80 degrees. However, in other embodiments, the spacing may be preferably about 60 degrees, depending on the spatial positioning of the at least three pairs of energy sources and detectors in the first plane.

The at least three energy sources and the at least three detectors in the first plane may be each located on a respective common arc in the first plane through the subject's body. In some embodiments, the three energy sources and three detectors are located on the same common arc in the first plane. In embodiments where the three energy sources and three detectors are located on different common arcs, the length of the common arc on which the energy sources are located preferably has a greater length than the common arc on which the detectors are located.

The at least four energy sources and the at least four detectors may be each spaced apart in one of an approximately T-shaped or inverted T-shaped configuration.

In some embodiments, at least one pair of energy sources and detectors is located in both of the first and second planes.

In some embodiments, the imaging device further includes at least four energy sources and at least four detectors. At least two pairs of energy sources and detectors may be spatially positioned in the first plane and at least two pairs of energy sources and detectors may be spatially positioned in the second plane.

The controller may be configured to acquire the images using at least four imaging angles through the region of the subject's body. At least two imaging angles may be provided in the first plane through the subject's body, and at least two imaging angles may be provided in the second plane through the subject's body.

The at least two imaging angles in the second plane may be spaced apart in a range of about 45 to 70 degrees. Preferably, the at least two imaging angles are spaced apart in a range of about 45 to 60 degrees or about 60 to 70 degrees. The spacing may be at an angle of about 45 degrees, about 50 degrees, about 55 degrees, about 60 degrees, about 65 degrees or about 70 degrees. Preferably, the spacing is about 60 degrees.

In some embodiments, at least two of the detectors are angled relative to the respective energy sources and at least two of the detectors are substantially aligned with the respective energy sources. The at least two detectors angled relative to the respective energy sources may indirectly face the respective energy sources and/or may be angled such that the imaging beams generated by the energy sources are not substantially orthogonal with the detectors. The at least two detectors substantially aligned with the respective energy sources may directly face the respective energy sources and/or may be substantially aligned such that the imaging beams generated by the energy sources are substantially orthogonal to the detectors. By providing at least two detectors angled relative to the respective energy sources enables a smaller, more compact imaging device that still allows for multiple images to be acquired at different angles through the subject's body.

The at least two energy sources and the at least two detectors in the second plane may be each located on a respective common arc in the second plane. In some embodiments, the two energy sources and two detectors are located on the same common arc in the second plane. In embodiments where the two energy sources and two detectors are located on different common arcs, the length of the common arc on which the energy sources are located preferably has a greater length than the common arc on which the detectors are located.

In some embodiments, the at least four energy sources and the at least four detectors are each spaced apart in an approximately diamond-shaped configuration. In other embodiments, the at least four energy sources and the at least four detectors are each spaced apart in an approximately square-shaped or rectangular-shaped configuration.

In some embodiments, the second plane is offset at an angle of about 70 to 90 degrees relative to the first plane. The second plane may be offset at an angle of about 70 degrees, about 75 degrees, about 80 degrees, about 85 degrees or about 90 degrees. The second plane may be offset at an angle of about 70 to 80 degrees or of about 80 to 90 degrees relative to the first plane. The second plane may be offset at an angle of about 80 degrees relative to the first plane.

In some embodiments, the second plane is offset at an angle of about 90 degrees relative to the first plane, such that the second plane and the first plane are substantially orthogonal. The first plane may be a transverse plane through the subject's body, and the second plane may be a sagittal plane through the subject's body.

The imaging device may be configured for accommodating the subject in an upright orientation between the energy sources and detectors. The subject may be in an upright seated position in the imaging device. Alternatively, the subject may be in an upright standing position in the imaging device.

The imaging device may be configured for accommodating the subject between the energy sources and detectors in a position that is closer to the detectors than the energy sources. The subject may not be centrally positioned between the detectors and energy sources in the imaging device and may instead be located in closer proximity to the detectors.

In some embodiments, the controller is configured to operate the energy sources and detectors to acquire a time series of in vivo images of the region of the subject's body simultaneously or at substantially the same time from each of the detectors. Thus, at least three time series of in vivo images may be acquired simultaneously or at substantially the same time from the at least three detectors. In some embodiments including four energy sources and four detectors, four time series of in vivo images may be acquired simultaneously or at substantially the same time from the four detectors. The imaging device may further include a processor configured to reconstruct a three-dimensional motion field based on the time series of images acquired from each of the detectors. The three-dimensional motion field may thus be reconstructed by the processor based on either three or four time series of images acquired from the detectors.

The imaging device may be configured for use with one or more of x-ray imaging, ultrasound imaging, and magnetic resonance imaging (MRI). The x-ray imaging may include fluoroscopic imaging and/or computed tomographic x-ray velocity (CTXV) imaging.

The region of the subject's body to be imaged may include at least part of the lungs of the subject. The imaging device may image part of the lung or the whole lung. The imaging device may also image both lungs of the subject. Alternatively, the region to be imaged may include part or the whole of the heart or brain of the subject. The region to be imaged may include parts of the body other than organs, including tissues, such as abdominal tissues.

Ideally, the subject's breathing is not restricted or controlled during image acquisition. The imaging device may be configured to acquire the images while the subject is breathing and preferably of a full single breath of the subject.

In another aspect, the present disclosure provides a method for acquiring a time series of in vivo images of a region of a subject's body. The method includes the step of providing an imaging device including at least three energy sources, at least three detectors for detecting energy from the at least three energy sources passing through the region of the subject's body located between the energy sources and detectors, and a controller configured to operate the energy sources and the detectors to acquire a time series of in vivo images of the region of the subject's body. At least two pairs of energy sources and detectors are spatially positioned around the subject's body in a first plane, and at least one pair of energy sources and detectors is spatially positioned around the subject's body in a second plane. The first plane and the second plane intersect through the region of the subject's body to be imaged. The method also includes the step of operating the controller to acquire the time series of in vivo images of the region of the subject's body.

In some embodiments, the method further includes the step of operating the controller to acquire a time series of in vivo images of the region of the subject's body simultaneously or at substantially the same time from each of the detectors. Thus, at least three time series of in vivo images may be acquired simultaneously or at substantially the same time from the at least three detectors. In some embodiments including four energy sources and four detectors, four time series of in vivo images may be acquired simultaneously or at substantially the same time from the four detectors. The method may further include the step of reconstructing, using a processor, a three-dimensional motion field based on the time series of images acquired from each of the detectors. The three-dimensional motion field may thus be reconstructed by the processor based on either three or four time series of images acquired from the detectors.

In some embodiments, the method further includes the step of prior to operating the controller to acquire the images, positioning the subject in the imaging device in an upright orientation between the energy sources and detectors. The subject may be positioned in an upright seated position in the imaging device. Alternatively, the subject may be positioned in an upright standing position in the imaging device.

The imaging device may be configured for use with one or more of x-ray imaging, ultrasound imaging, and magnetic resonance imaging (MRI). The x-ray imaging may include fluoroscopic imaging and/or computed tomographic x-ray velocity (CTXV) imaging.

The region of the subject's body to be imaged may include at least part of the lungs of the subject. The imaging device may image part of the lung or the whole lung. The imaging device may also image both lungs of the subject. Alternatively, the region to be imaged may include part or the whole of the heart or brain of the subject. The region to be imaged may include parts of the body other than organs, including tissues, such as abdominal tissues.

Ideally, the subject's breathing is not restricted or controlled during image acquisition. The imaging device may be configured to acquire the images while the subject is breathing and preferably of a full single breath of the subject.

Also disclosed herein is an imaging device for acquiring a time series of images of a region of a subject's body. The imaging device includes at least three energy sources, at least three detectors for detecting energy from the at least three energy sources passing through the region of the subject's body located between the energy sources and detectors, and a controller configured to operate the energy sources and detectors to acquire a time series of images of the region of the subject's body. At least two pairs of energy sources and detectors are spatially positioned around the subject's body in a first plane, and at least one pair of energy sources and detectors is spatially positioned around the subject's body in a second plane. The first plane and the second plane intersect through the region of the subject's body to be imaged. The imaging device may provide in vivo imaging of the region of the subject's body, and provide a time series of in vivo images. The region to be imaged may include at least part of the lungs of the subject.

Also disclosed herein is a method for acquiring a time series of images of a region of a subject's body. The method includes the step of providing an imaging device including at least three energy sources, at least three detectors for detecting energy from the at least three energy sources passing through the region of the subject's body located between the energy sources and detectors, and a controller configured to operate the energy sources and the detectors to acquire a time series of images of the region of the subject's body. At least two pairs of energy sources and detectors are spatially positioned around the subject's body in a first plane, and at least one pair of energy sources and detectors is spatially positioned around the subject's body in a second plane. The first plane and the second plane intersect through the region of the subject's body to be imaged. The method also includes the step of operating the controller to acquire the time series of images of the region of the subject's body. The method may provide in vivo imaging of the region of the subject's body, and acquire a time series of in vivo images. The region to be imaged may include at least part of the lungs of the subject.

BRIEF DESCRIPTION OF DRAWINGS

The disclosure will now be described in greater detail with reference to the accompanying drawings in which like features are represented by like numerals. It is to be understood that the embodiments shown are examples only and are not to be taken as limiting the scope of the disclosure as defined in the claims appended hereto.

FIG. 14 is a flow chart showing steps in a method for imaging according to some embodiments of the disclosure.

DETAILED DESCRIPTION

Figure 1:
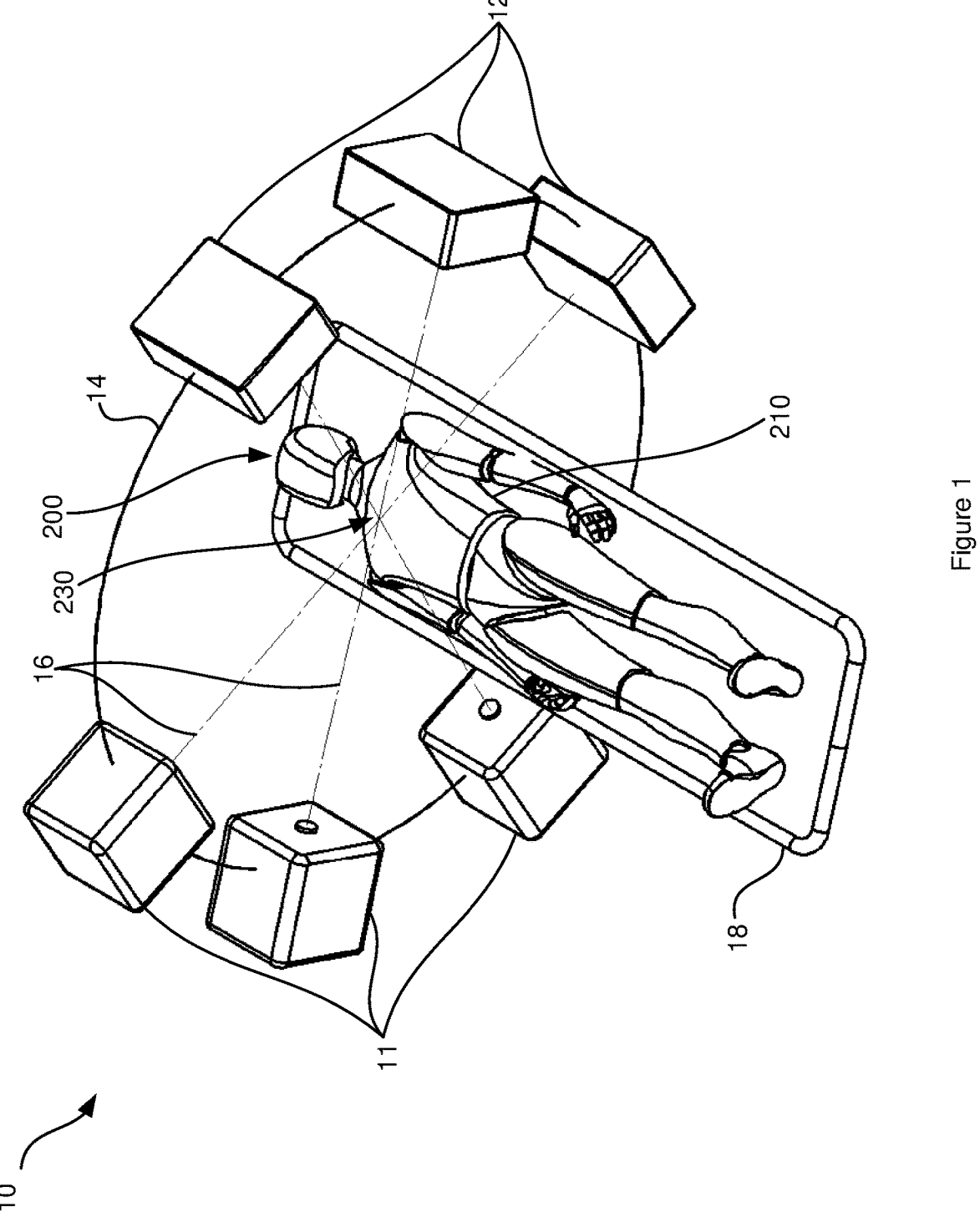
FIG. 1 is a perspective view of a system for imaging a region of a subject's body, where the system includes three energy sources and three detectors positioned in a common plane and located on a common arc around the subject's body which is located in a supine position on a tray during scanning.

Embodiments of the disclosure are discussed herein by reference to the drawings which are not to scale and are intended merely to assist with explanation of the disclosure. Reference herein to a subject may include a human or animal subject, or a human or animal patient on which medical procedures are performed and/or screening, monitoring and/or diagnosis of a disease or disorder is performed. In relation to animal patients, embodiments of the disclosure may also be suitable for veterinary applications. The terms subject and patient, and imaging device and scanner, respectively, are used interchangeably throughout the description and should be understood to represent the same feature of embodiments of the disclosure. Reference herein is also provided to anatomical planes of a subject's body, including the transverse or horizontal plane, the sagittal or vertical plane, and the coronal or frontal plane through the subject's body.

Embodiments of the disclosure are directed to an imaging device and method for acquiring in vivo images of a region of a subject's body, and for acquiring multiple images from different perspectives or imaging angles through the subject's body. Ideally, the multiple images from different perspectives or imaging angles may be acquired simultaneously or at substantially the same time. Preferably, the region to be imaged includes one or both lungs of the subject, or part of a lung of the subject. Alternatively, the region to be imaged may include part of or the whole of the heart or brain of the subject. Other organs or regions of the subject's body may also be suitable for functional imaging, such as those in which dynamic in vivo changes are detectable including changes in motion, location and/or size, during breathing or other physiological processes of the subject's body, as would be appreciated by a person skilled in the art.

The images acquired are ideally of the type suitable for XV processing in accordance with the techniques described in International Patent Application No. PCT/AU2010/001199 filed on 16 Sep. 2010 and published as WO 2011/032210 A1 on 24 Mar. 2011 filed in the name of Monash University, and International Patent Application No. PCT/AU2015000219 filed on 14 Apr. 2015 and published as WO 2015/157799 A1 on 22 Oct. 2015 filed in the name of 4Dx Pty Ltd, the entire disclosures of both of which are incorporated herein by this reference. Thus, the images acquired may be processed using the XV technique described in those disclosures to provide a three-dimensional motion field of the region imaged, which preferably represents the three spatial dimensions over time of the region imaged. In the context of imaging of the lungs, this allows for motion of the lungs to be measured throughout the respiratory cycle, enabling evaluation of lung function at each region within the lung in fine spatial and temporal detail. Similar images may be obtained for other regions of the subject's body, including the heart or brain, or other organs or regions in which dynamic in vivo changes are detectable.

The imaging device may be suitable for X-ray imaging techniques, together with other imaging methods that do not involve the use of X-rays. In particular, the imaging device and method may be configured for one or more of x-ray imaging, ultrasound imaging, and magnetic resonance imaging (MRI). The imaging device and related method may be configured for use with static or dynamic x-ray imaging techniques. Dynamic x-ray imaging techniques may include fluoroscopic imaging and/or computed tomographic x-ray velocity (CTXV) imaging. The imaging device 100 and method 300 are preferably configured for fluoroscopic imaging. The CTXV imaging technique which also uses fluoroscopy is described in more detail in previously mentioned International Patent Publication Nos. WO 2011/032210 A1 and WO 2015/157799 A1.

Embodiments of the disclosure are directed to an inventive imaging device 100 for acquiring a time series of in vivo images of a region 230 of a subject's body 210, as shown in the embodiments of FIGS. 3 to 13. The imaging device 100 includes at least three energy sources 110 (denoted as 110A, 110B) and at least three detectors 120 (denoted as 120A, 120B) for detecting energy from the at least three energy sources 110 passing through the region 230 of the subject's body 210 located between the energy sources 110 and detectors 120. At least two pairs of energy sources and detectors 110A, 120A are spatially positioned around the subject's body 210 in a first plane, and at least one pair of energy sources and detectors 110B, 120B is spatially positioned around the subject's body 210 in a second plane. The first plane and the second plane intersect through the region 230 of the subject's body 210 to be imaged (see also FIG. 5). The imaging device 100 also includes a controller 140 configured to operate the energy sources 110A, 110B and detectors 120A, 120B to acquire a time series of in vivo images of the region 230 of the subject's body 210.

In embodiments of the disclosure, the energy sources 110 and detectors 120 are stationary during scanning, adopting a fixed position in the imaging device 100. The spatial arrangement of the energy sources 110 and detectors 120 is an important aspect of the disclosure as will be described in relation to the embodiments of FIGS. 3 to 12. The spatial arrangement enables multiple images to be acquired without the need to rotate the energy sources 110 and detectors 120 around the subject 200 during imaging. Furthermore, the spatial arrangement enables a more compact scanner to be provided without comprising on image quality.

Preferably, the region 230 to be imaged may include at least part of a lung of the subject 200, and the duration of imaging may be based on a subject's single breath. Desirably, the imaging device 100 enables multiple time series of images to be acquired of either part or a single breath of the subject 200. This may include inspiration, expiration or both inspiration and expiration for a full breath. Preferably, the imaging device 100 enables multiple time series to be acquired of a full single breath of the subject 200.

In some embodiments, the controller 140 is configured to acquire the images using at least three imaging angles through the region 230 of the subject's body 210. At least two imaging angles may be provided in the first plane through the subject's body 210, and at least one imaging angle may be provided in the second plane through the subject's body 210. The spatial arrangement and positioning of the pairs of energy sources and detectors to provide the at least three imaging angles will be discussed in more detail below in relation to the embodiment of FIG. 3. In the embodiments of FIGS. 4 to 12, the controller 140 is configured to acquire the images using at least four imaging angles through the region 230 of the subject's body 210, with at least two imaging angles being provided in each of the first and second planes through the subject's body 210.

Embodiments of the disclosure advantageously acquire a time series of in vivo images of the region 230 of the subject's body 210. The embodiments of the disclosure include at least three pairs of energy sources 110 and detectors 120 (see FIG. 3) or preferably, four pairs of energy sources 110 and detectors 120 (see FIGS. 4 to 12). This enables at least three, and preferably four, time series of in vivo images to be acquired during scanning. By acquiring a time series of images from multiple angles it is possible to provide dynamic imaging of the subject's body 210. In particular, embodiments of the disclosure may be suitable for functional imaging, such as those in which dynamic in vivo changes are detectable including changes in motion, location and/or size of organs or regions of the body, during breathing or other physiological processes of the subject's body 210, as would be appreciated by a person skilled in the art. This will be described in more detail in relation to inventive method 300 and processing of the acquired images using XV techniques.

Figure 2:
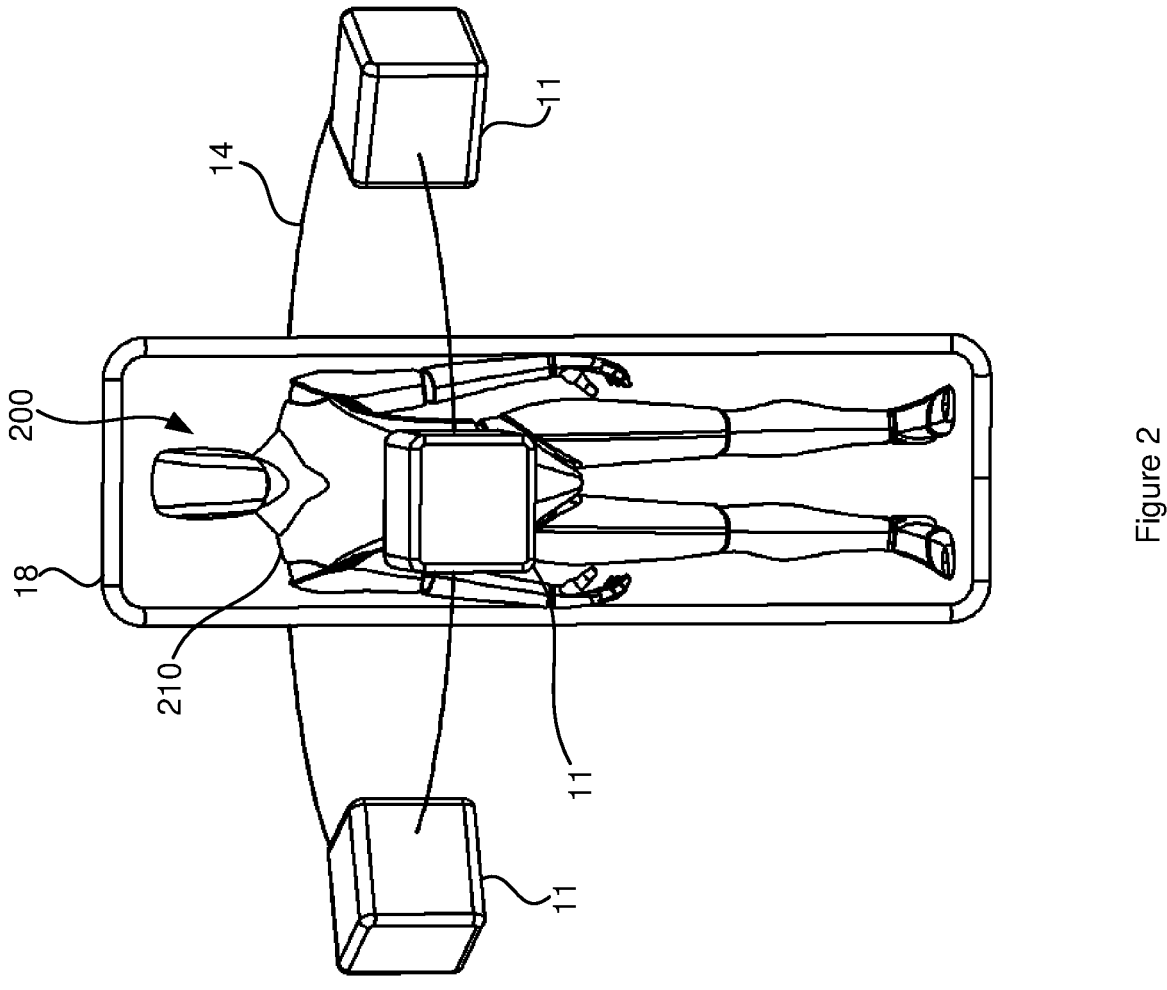
FIG. 2 is a plan view of the system of FIG. 1 showing three energy sources in a common plane and located on a common arc around the subject's body, and omitting the detectors for clarity.

Advantageously, embodiments of the disclosure provide at least one pair of energy sources and detectors 110B, 120B which is spatially positioned around the subject's body 210 in the second plane offset at an angle relative to the first plane having at least two pairs of energy sources and detectors 110A, 120A. By providing at least one pair of energy sources and detectors 110B, 120B being offset in a second plane relative to the other energy sources and detectors 110A, 120A, this allows the inventive imaging device 100 to be more compact as the energy sources and detectors can be located more closely together instead of within the same plane on a common arc 14 of the system 10 as shown in FIGS. 1 and 2. Although the inventive imaging device 100 is more compact, the device 100 still acquires images suitable for use with the XV technology with multiple images being acquired from different perspectives or imaging angles through the region 230 of the subject's body 210, and that optionally reduces the use of X-rays and/or enhances scan quality. Ideally, the multiple images from different perspectives or imaging angles may be acquired simultaneously or at substantially the same time due to the spatial arrangement of the energy sources 110A, 110B and detectors 120A, 120B.

It has not been previously envisioned to provide at least one pair of energy sources and detectors offset on a different plane relative to the remaining pairs of energy sources and detectors in a medical scanner. This arrangement would be considered counterintuitive in view of the system 10 illustrated in FIGS. 1 and 2 or other typical CT scanners or those employing CTXV techniques. A skilled addressee would understand that optimal image acquisition should be obtained by equally spacing the detectors and sources circumferentially across a 180 degrees angle of the patient's body (or optionally 360 degrees as shown in FIGS. 1 and 2) to provide dynamic in vivo imaging capability. Thus, a skilled addressee would consider that spacing of the energy sources and detectors into a smaller angle would provide insufficient imaging data. Furthermore, a skilled addressee would also appreciate that modified software for processing the imaging data would be required for this inventive arrangement of the energy sources and detectors, thus discouraging this arrangement from being pursued.

Figure 3:
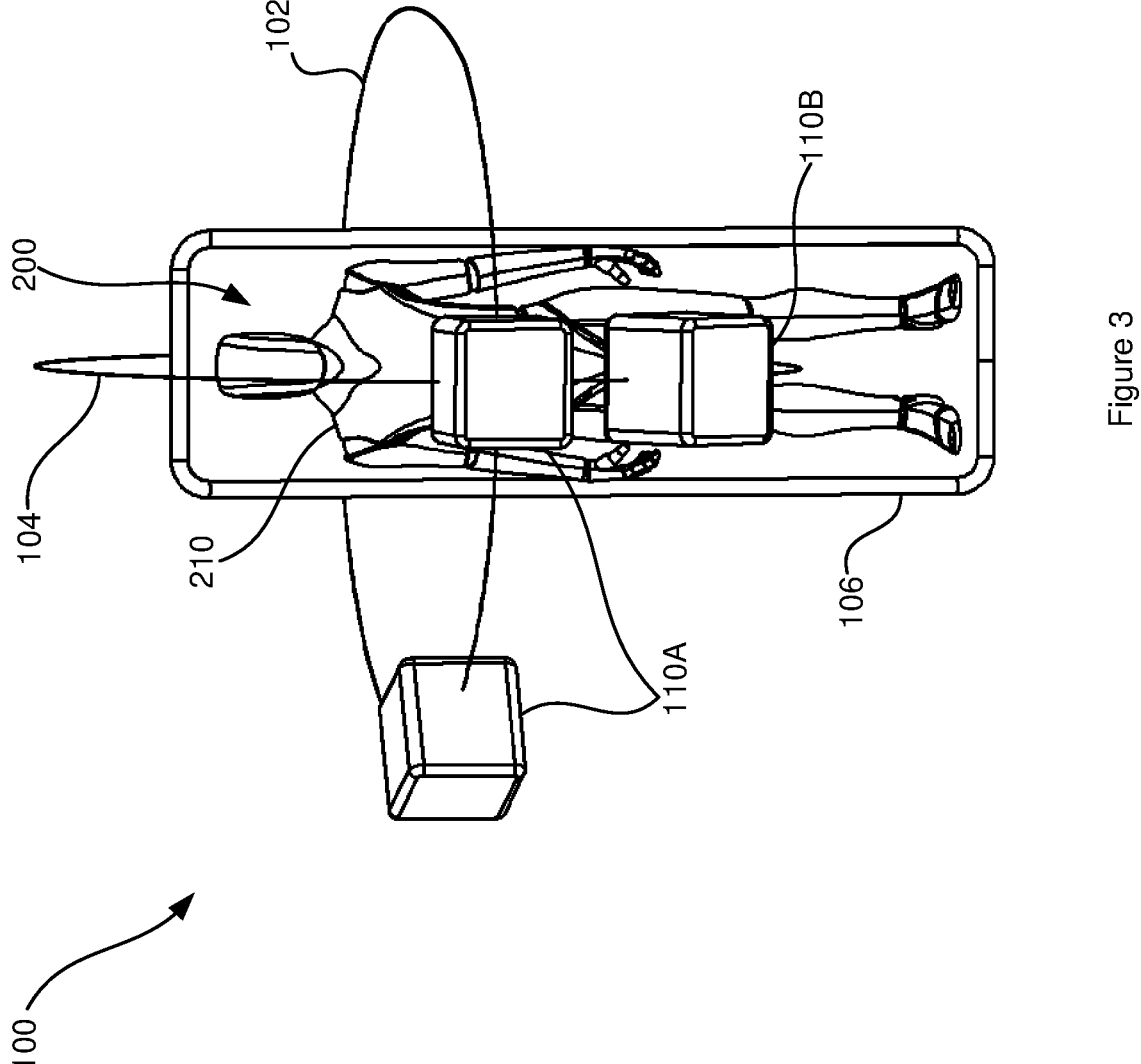
FIG. 3 is a plan view of an imaging device according to some embodiments of the disclosure, showing three energy sources spatially positioned around a subject's body in an approximately triangular-shaped or L-shaped configuration, where the subject's body is oriented in a supine position and the detectors have been omitted for clarity.

FIG. 3 is a plan view showing an imaging device 100 according to some embodiments of the disclosure, including three energy sources 110A, 110B which are spatially positioned around a subject's body 210 oriented in a supine position on a tray or bed 106. The corresponding detectors have been omitted from this figure for clarity and would be located behind the tray 106 underneath the subject's body 210. The three energy sources 110A, 110B are positioned in a substantially triangular-shaped or L-shaped configuration, although other configurations are possible including irregular shapes. Two energy sources 110A are located on a common first arc 102 in a first plane through the subject's body 210. Preferably, the first plane is a transverse or horizontal plane through the subject's body 210 as shown in FIG. 3. The energy source 110B is located on a second arc 104 in a second plane of the subject's body 210. A central energy source 110A positioned above the energy source 110B is located on both of the first arc 102 and second arc 104, thus being positioned in both of the first and second planes. Preferably, the second plane is a sagittal or vertical plane through the subject's body 210 as shown in FIG. 3. A similar arrangement is provided by the corresponding detectors 120A, 120B (omitted, see e.g., FIG. 5).

In this embodiment, the controller 140 may be configured to acquire the images using three imaging angles or perspectives through the region 230 of the subject's body 210. The imaging angles may be defined by the spatial positioning of the pairs of energy sources and detectors around the subject's body 210. Two imaging angles may be provided in the first plane through the subject's body 210 by the provision of two pairs of energy sources and detectors 110A, 120A (detectors omitted) located on the first arc 102. Furthermore, one additional imaging angle may be provided in the second plane through the subject's body 210 by the provision of one pair of energy sources and detectors 110B, 120B (detectors omitted) located on the second arc 104. The imaging angles may be defined by the imaging or projection line connecting the energy source 110 and corresponding detector 120, which passes through the region 230 of the subject's body 210 to be imaged, as shown by imaging beams 116 in the embodiments of FIGS. 5 to 12 (see also e.g., imaging beams 16 of FIGS. 1 and 2).

The two imaging angles in the first plane defined by the imaging lines through the subject's body 210 connecting the two pairs of energy sources and detectors 110A, 120A may preferably be spaced apart in a range of about 45 to 90 degrees. Preferably, the two imaging angles are spaced apart in a range of about 45 to 70 degrees or about 70 to 90 degrees, or about 45 to 60 degrees, about 60 to 70 degrees, about 70 to 80 degrees or about 80 to 90 degrees. The spacing may be about 45 degrees, about 50 degrees, about 55 degrees, about 60 degrees, about 65 degrees, about 70 degrees, about 75 degrees, about 80 degrees, about 85 degrees or about 90 degrees. Preferably, the spacing is about 80 degrees. However, in other embodiments, the spacing may be preferably about 60 degrees, depending on the spatial positioning of the two pairs of energy sources and detectors in the first plane.

The two energy sources 110A and the two detectors 120A (not shown) in the first plane may be each located on a respective common arc in the first plane, which may be the same common arc, namely the first arc 102 as shown in FIG. 3. Similarly, the two energy sources 110A (central source), 110B and the two detectors 120A, 120B (not shown) in the second plane may each be located on a respective common arc in the second plane, which may be the same common arc, namely the second arc 104 as shown in FIG. 3. Thus, in this embodiment, the subject 200 may be positioned centrally within the imaging device 100 and equidistant from each of the energy sources 110A, 110B and detectors 120A, 120B.

The imaging process of FIG. 3 is more clearly demonstrated by the embodiments of FIGS. 5 to 12 which include four energy sources 110A, 110B and four detectors 120A, 120B. Each energy source 110A, 110B produces an imaging beam 116 which passes through the region 230 to be imaged and a projection is acquired by a corresponding detector 120A, 120B. Each energy source 110A, 110B is angled towards the region 230 to be imaged so that the imaging beams 116 are received through the same volume, which is the area of interest being imaged by all sources 110A, 110B, although from different angles or perspectives.

In the embodiments of FIGS. 3 to 9, the energy sources 110A, 110B are angled towards the region 230 to be imaged, and the corresponding detectors 120A, 120B are angled towards the respective energy sources 110A, 110B in order to acquire the images. Each of the detectors 120A, 120B are substantially aligned with the respective energy sources 110A, 110B, and in fact, directly face the respective energy sources 110A, 110B. The detectors 120A, 120B are substantially aligned with the respective energy sources such that the imaging beams 116 generated by the respective energy sources 110A, 110B are substantially orthogonal to the detectors 120A, 120B.

Figure 10:
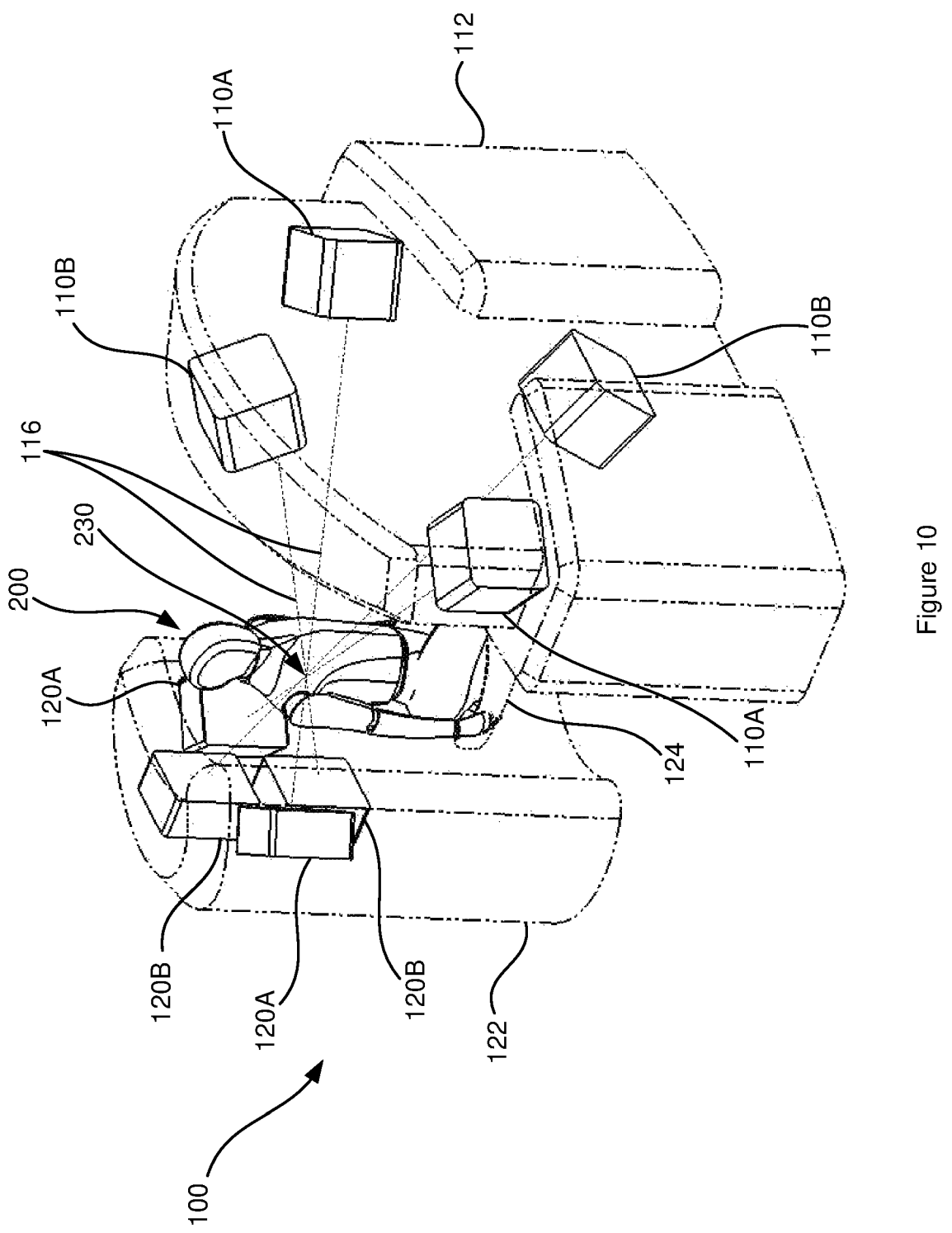
FIG. 10 is a perspective view of another imaging device according to some embodiments of the disclosure, showing a similar arrangement to FIG. 7 except that two of the detectors are angled relative to the respective energy sources, and are co-planar and vertically oriented relative to one another.
Figure 11:
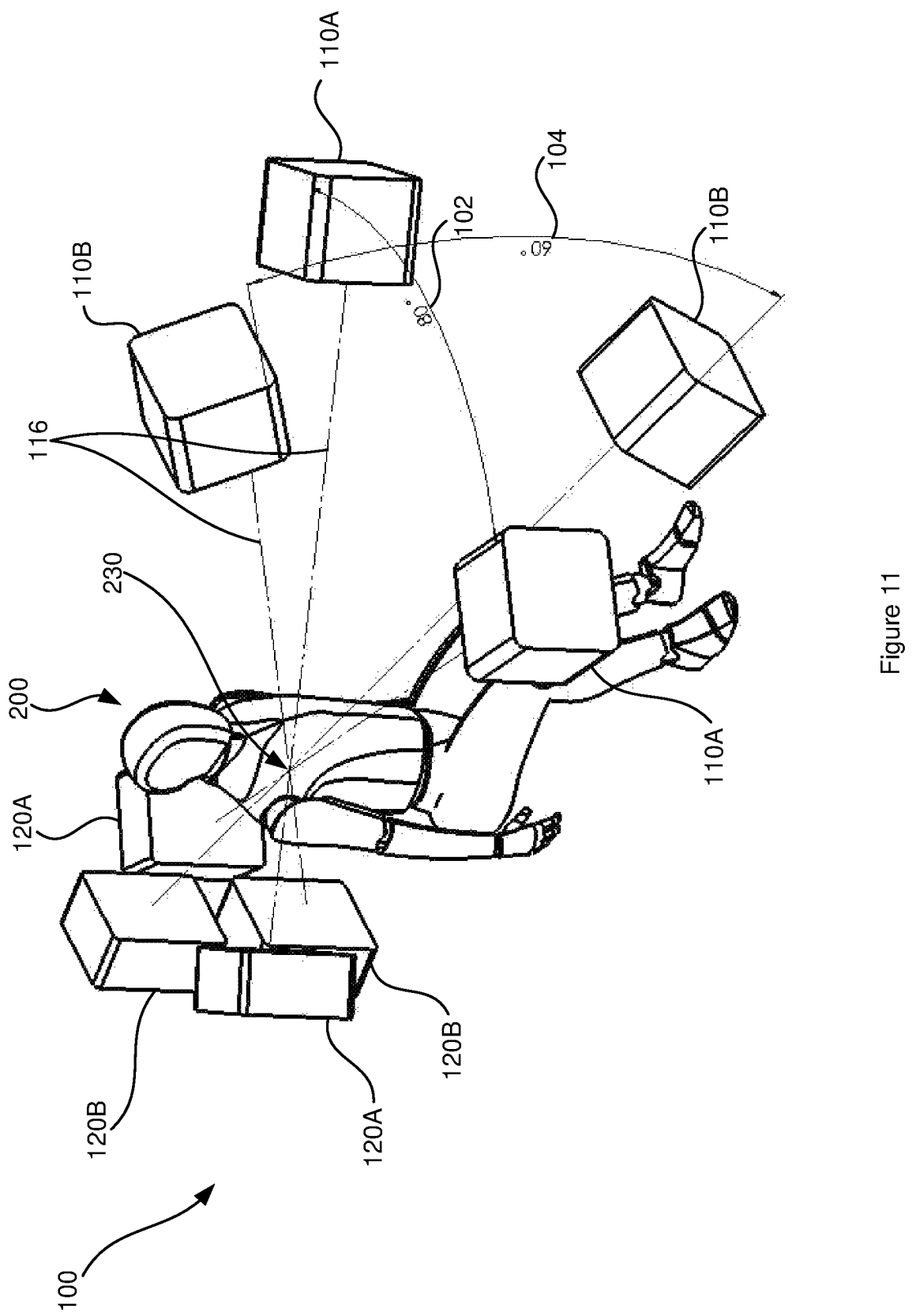
FIG. 11 is a perspective view of the imaging device of FIG. 10 excluding the exemplary detector unit and source unit for clarity.
Figure 12:
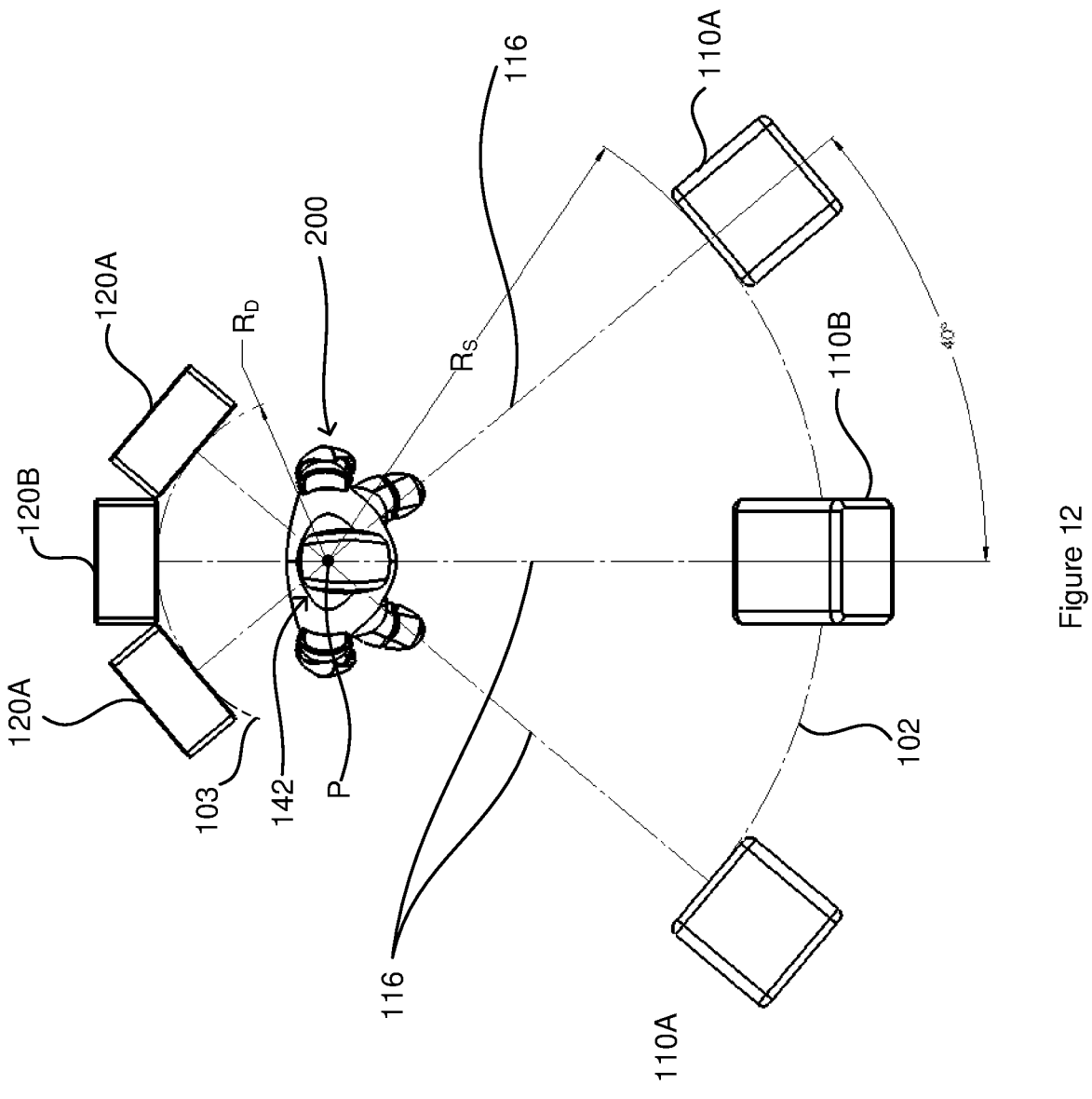
FIG. 12 is a plan view of the imaging device of FIG. 10 excluding the exemplary detector unit and source unit for clarity.

In contrast, the embodiments of FIGS. 10 to 12 show an alternative arrangement in which two detectors 120B are angled relative to the respective energy sources 110B. The detectors 120B may indirectly face the respective energy sources 110B. The detectors 120B may be angled such that the imaging beams 116 generated by the energy sources 110B are not substantially orthogonal with the detectors 120B. Furthermore, the detectors 120B are not located on a common arc in the second plane (in contrast to the detectors 120A on arc 103 as shown in FIG. 12). However, all of the energy sources 110A, 110B are located on common arc 102 or 104. Nonetheless, the two detectors 120B are spatially positioned and angled relative to the respective energy sources 110B such that they still receive the imaging beam 116 passing through the region 230 from the respective energy sources 110B.

Various embodiments of the spatial arrangements of the energy sources 110 and detectors 120 of the inventive imaging device 100 will now be described in more detail with respect to FIGS. 4 to 12.

Figure 4:
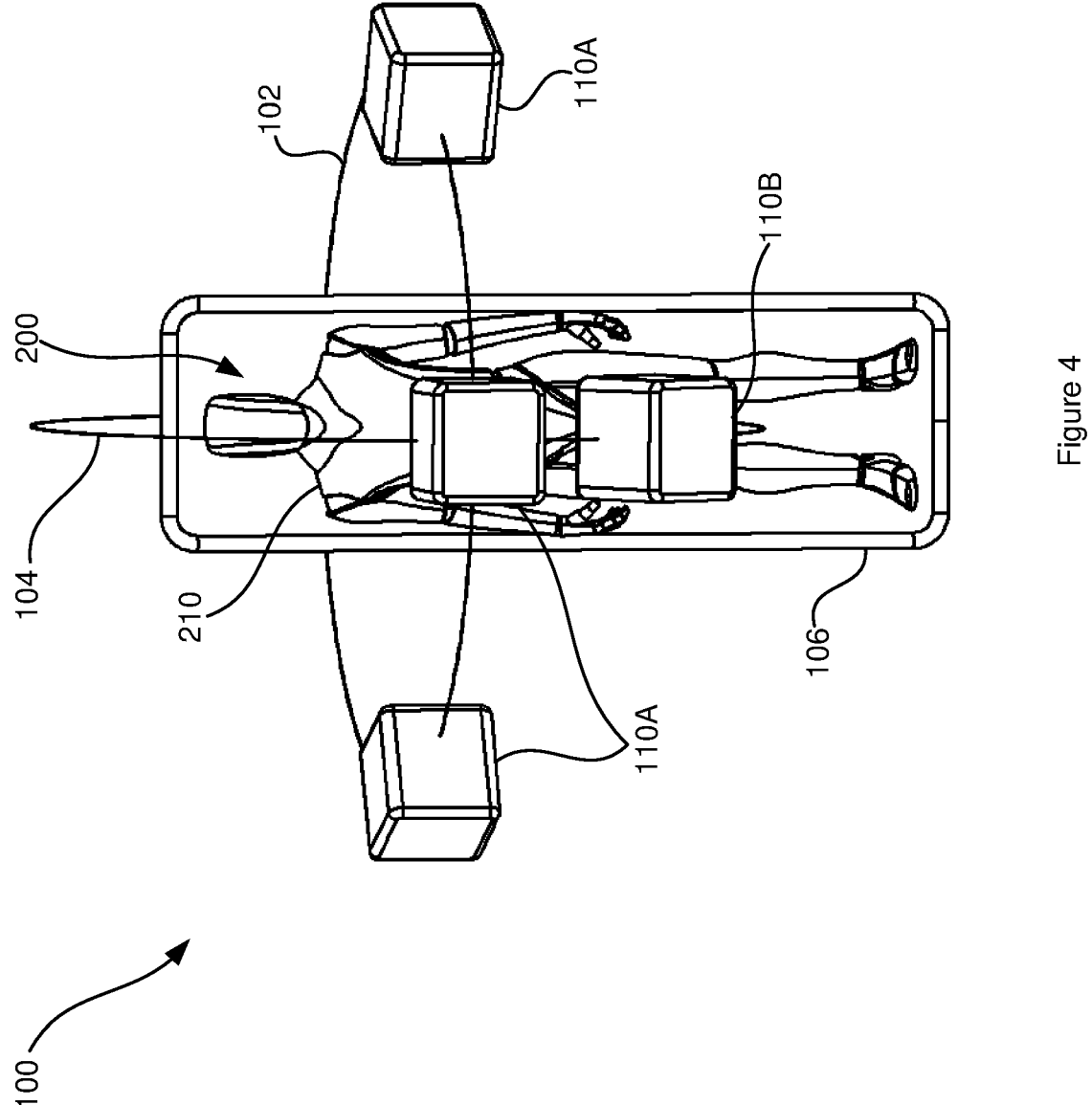
FIG. 4 is a plan view of another imaging device according to some embodiments of the disclosure, showing four energy sources spatially positioned around a subject's body in an approximately T-shaped configuration, where the subject's body is oriented in a supine position and the detectors have been omitted for clarity.

FIG. 4 is a plan view showing another imaging device 100 according to some embodiments of the disclosure, including four energy sources 110A, 110B which are spatially positioned around a subject's body 210 oriented in a supine position on a tray or bed 106. The corresponding detectors have been omitted from this figure for clarity and would be located behind the tray 106 underneath the subject's body 210. The four energy sources 110A, 110B are positioned in a substantially T-shaped configuration. Three energy sources 110A are located on a common first arc 102 in a first plane through the subject's body 210. Preferably, the first plane is a transverse or horizontal plane of the subject's body 210 as shown in FIG. 4. The energy source 110B is located on a second arc 104 in a second plane of the subject's body 210. The central energy source 110A on the first arc 102 is also positioned on the second arc 104, and thus is provided in both of the first and second planes. Preferably, the second plane is a sagittal or vertical plane through the subject's body 210 as shown in FIG. 4. A similar arrangement may be provided by the corresponding detectors 120A, 120B (omitted, see e.g., FIG. 5).

In this embodiment, the controller 140 may be configured to acquire the images using four imaging angles or perspectives through the region 230 of the subject's body 210. The imaging angles may be defined by the spatial positioning of the pairs of energy sources and detectors around the subject's body 210. Three imaging angles may be provided in the first plane through the subject's body 210 by the provision of three pairs of energy sources and detectors 110A, 120A (detectors omitted) located on the first arc 102. Furthermore, one additional imaging angle may be provided in the second plane through the subject's body 210 by provision of one pair of energy sources and detectors 110B, 120B (detectors omitted) located on the second arc 104. The imaging angles may be defined by the imaging or projection line connecting the energy source 110 and detector 120, which passes through the region 230 of the subject's body 210 to be imaged, as shown by imaging lines 116 in the embodiments of FIGS. 5 to 12.

The three imaging angles in the first plane defined by the imaging lines through the subject's body 210 connecting the three pairs of energy sources and detectors 110A, 120A may preferably be each spaced apart in a range of about 45 to 90 degrees. Preferably, the three imaging angles are each spaced apart in a range of about 45 to 70 degrees or about 70 to 90 degrees, or about 45 to 60 degrees, about 60 to 70 degrees, about 70 to 80 degrees or about 80 to 90 degrees. The spacing may be about 45 degrees, about 50 degrees, about 55 degrees, about 60 degrees, about 65 degrees, about 70 degrees, about 75 degrees, about 80 degrees, about 85 degrees or about 90 degrees. Preferably, the spacing is about 80 degrees. However, in other embodiments, the spacing may be preferably about 60 degrees, depending on the spatial positioning of the three pairs of energy sources and detectors in the first plane.

The three energy sources 110A and the three detectors 120A (not shown) in the first plane may be each located on a respective common arc in the first plane, which may be the same common arc, namely the first arc 102 as shown in FIG. 4. Similarly, the two energy sources 110A (central source), 110B and the two detectors 120A, 120B (not shown) in the second plane may each be located on a respective common arc in the second plane, which may be the same common arc, namely the second arc 104 as shown in FIG. 4. Thus, in this embodiment and similar to FIG. 3, the subject 200 may be positioned centrally within the imaging device 100 and equidistant from each of the energy sources 110A, 110B and detectors 120A, 120B. The detectors 120A, 120B are substantially aligned with the respective energy sources 110A, 110B in this embodiment and are positioned orthogonally to the imaging beams 116 generated by the respective energy sources 110A, 110B. However, the detectors 120A, 120B may not be substantially aligned and instead angled relative to the respective energy sources 110A, 110B as will be described in relation to FIGS. 10 to 12.

In the embodiments of FIGS. 3 and 4, the second plane is orthogonal to the first plane such that the first and second arcs 102 and 104 are at 90 degrees relative to one another and the single energy source 110B is aligned below the central energy source 110A on the second arc 104. However, in other embodiments, the second plane may be offset at an angle in a range of between about 70 to 90 degrees relative to the first plane. Preferably, the offset angle is about 80 degrees. Thus, the energy source 110B may be angled relative to the central energy source 110A by an angle of about 20 degrees to the left or right of a vertical or sagittal plane through the subject's body, or preferably, about 10 degrees to the left or right of the vertical or sagittal plane. The three energy sources 110A, 110B (and three detectors 120A, 120B not shown) of FIG. 3 may not form an exact L-shaped configuration, and instead may form a substantially L-shaped configuration due to angling of the energy source 110B relative to the central energy source 110A. Similarly, the four energy sources 110A, 110B (and four detectors 120A, 120B not shown) of FIG. 4 may not form an exact T-shaped configuration as the vertical line of the 'T' may be angled relative to the horizontal line of the 'T', and instead may form a substantially T-shaped configuration due to angling of the energy source 110B relative to the central energy source 110A.

In other embodiments, the energy source 110B may be aligned above the central energy source 110A on the second arc 104 (not shown) in the embodiments of FIGS. 3 and 4. In relation to FIG. 4, the energy sources 110A, 110B and detectors (not shown) may form an inverted T-shaped configuration. The energy source 110B of FIGS. 3 and 4 may be angled relative to the central energy source 110A by an angle of about 20 degrees to the left or right of a vertical or sagittal plane through the subject's body, or preferably, about 10 degrees to the left or right of the vertical or sagittal plane. Thus, the four energy sources 110 may not form an exact inverted T-shaped configuration due to the angling of the energy source 110B. By varying the angles of the individual sources 110A, 110B and detectors 120A, 120B, various shaped configurations may be produced, including irregular or asymmetric shapes as will be described below.

Although not shown in FIG. 3, three corresponding detectors would also be provided in the imaging device 100, where the three detectors form an approximately triangular-shaped or L-shaped configuration. Similarly, although not shown in FIG. 4, four corresponding detectors would also be provided in the imaging device 100, where the four detectors may also form an approximately T-shaped or inverted T-shaped configuration.

Although FIGS. 3 and 4 depict offset angles of the second plane relative to the first plane angles of about 90 degrees (and preferably between about 70 to about 90 degrees), embodiments of the disclosure are not limited to these angles. The second plane may be offset at an angle of about 70 degrees, about 75 degrees, about 80 degrees, about 85 degrees or about 90 degrees. The second plane may be offset at an angle of about 70 to 80 degrees or of about 80 to 90 degrees relative to the first plane. The second plane may be offset at an angle of about 80 degrees relative to the first plane.

The energy sources 110A on the first arc 102 may also be spaced further apart up to 180 degrees circumferentially around the subject's body 210. In an alternative arrangement, the energy sources 110A may be spaced apart beyond 180 degrees such that one energy source 110A is located behind the subject's body 210 and a corresponding detector 120A is located in front of the subject's body 200. However, it is preferable that the energy sources 110A, 110B are closely positioned in order to provide a more compact scanner 100. Furthermore, the configuration of the energy sources 110A, 110B is also reflected in the corresponding arrangement of the detectors 120 (not shown). Thus, the detectors 120 are also ideally closely positioned in order to provide a more compact scanner 100. This will be explained in more detail in relation to an exemplary source unit 112 and detector unit 122 as shown and described with respect to FIGS. 7, 10 and 13.

Figure 5:
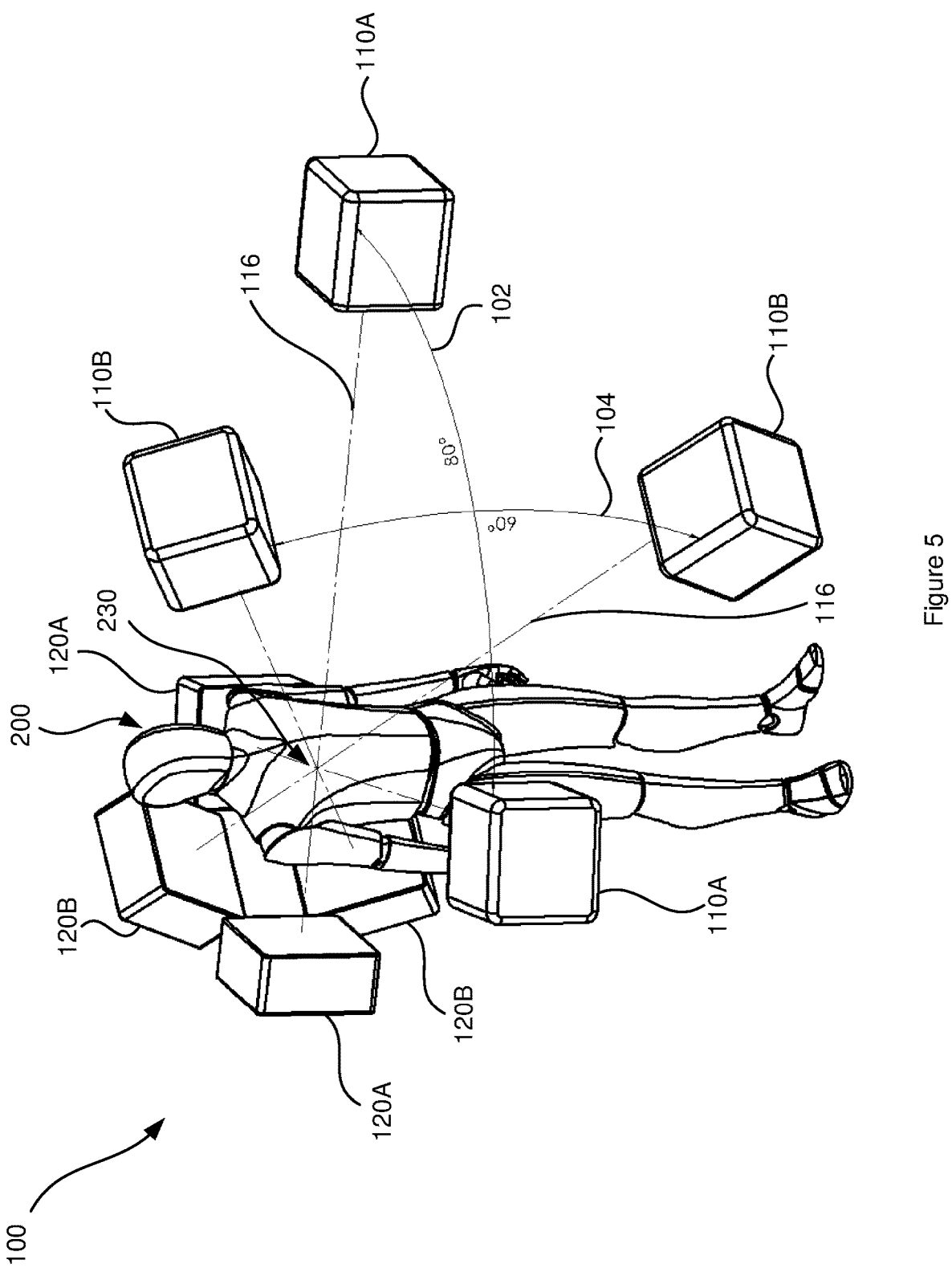
FIG. 5 is a perspective view of another imaging device according to some embodiments of the disclosure, showing four energy sources and four detectors each spatially positioned around a subject's body in an approximately diamond-shaped configuration, where the subject's body is oriented in an upright standing position in the scanner.

FIG. 5 is a perspective view of another imaging device 100 according to some embodiments of the disclosure, showing four energy sources 110 (denoted as 110A, 110B) and four detectors 120 (denoted as 120A, 120B) each spatially positioned around a subject's body 210 in a diamond-shaped configuration, where the subject's body 210 is oriented in an upright standing position in the scanner 100. The imaging device 100 includes two pairs of energy sources and detectors 110A, 120A and two pairs of energy sources and detectors 110B, 120B. The two pairs of energy sources and detectors 110A, 120A are spatially positioned in a first plane around the subject's body 210. The first plane is preferably a transverse or horizontal plane through the subject's body 210 as shown in FIG. 5. The two pairs of energy sources and detectors 110B, 120B are spatially positioned in a second plane around the subject's body 210. The second plane is preferably a sagittal or vertical plane through the subject's body 210. As shown in FIG. 5, the first and second planes intersect through the region 230 of the subject's body 210 to be imaged, as indicated by the intersection of imaging beams 116 between the respective energy source and detector pairs.

In this embodiment, the controller 140 may be configured to acquire the images using four imaging angles or perspectives through the region 230 of the subject's body 210. Two imaging angles may be provided in the first plane through the subject's body 210 by the provision of two pairs of energy sources and detectors 110A, 120A. Furthermore, two imaging angles may be provided in the second plane through the subject's body 210 by the provision of two pairs of energy sources and detectors 110B, 120B. The imaging angles may be defined by the imaging or projection lines connecting the energy sources 110 and detectors 120, which pass through the region 230 of the subject's body 210 to be imaged, as indicated by the imaging beams 116.

In the embodiments shown in FIGS. 5 to 12 which include four energy sources and four detectors, the energy sources 110A, 110B and detectors 120A, 120B are not provided on the same common arcs 102, 104 in the first and second planes in contrast to the embodiments of FIGS. 3 and 4. This is because the imaging devices 100 of FIGS. 3 and 4 enable the subject 200 to be centrally located between the energy sources 110 and detectors 120, whereas the imaging devices 100 of FIGS. 5 to 12 are configured to accommodate the subject 200 between the energy sources 110 and detectors 120 in a position that is closer to the detectors 120 than the energy sources 110.

Figure 7:
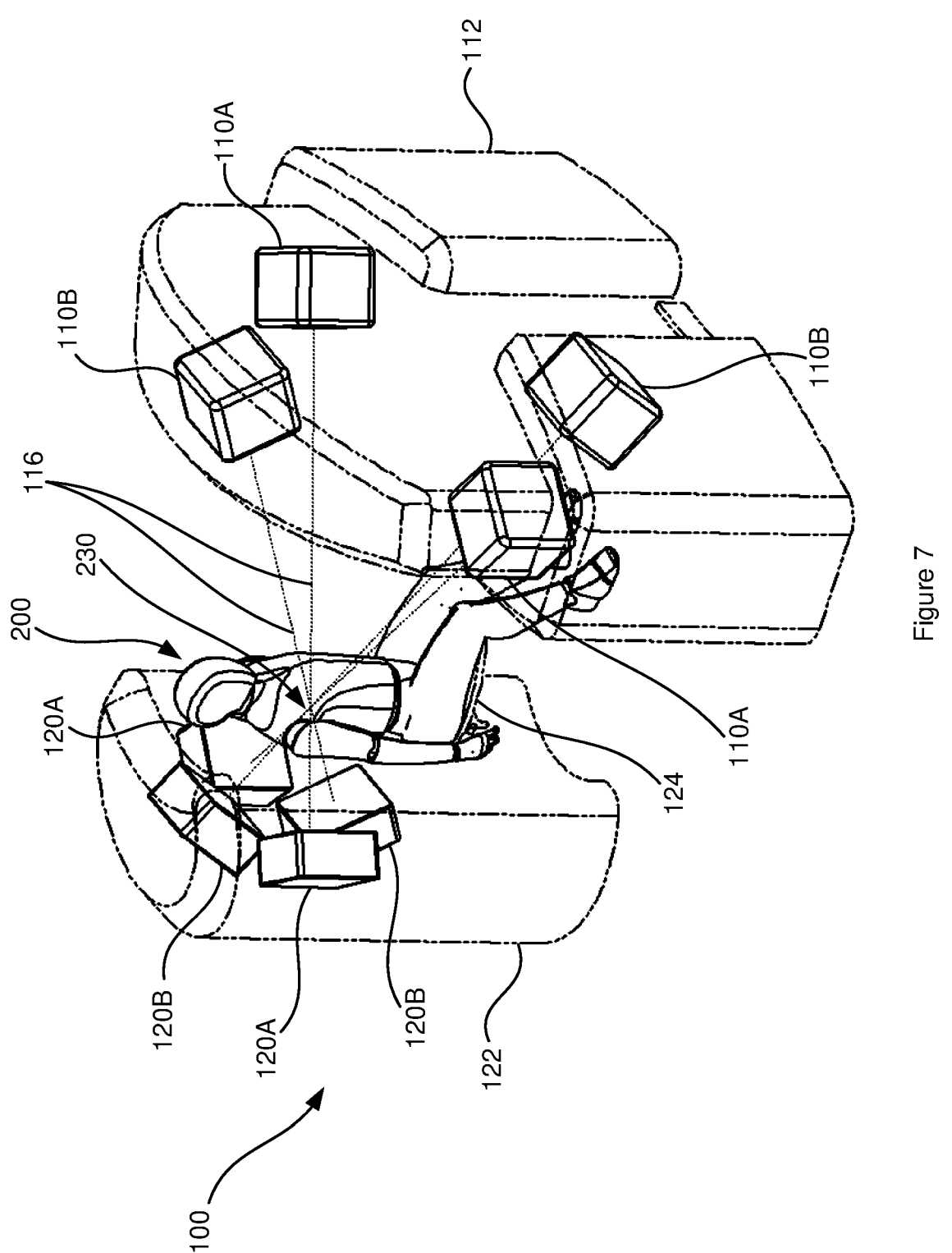
FIG. 7 is a perspective view of another imaging device according to some embodiments of the disclosure, showing four energy sources positioned in an exemplary source unit and four detectors positioned in an exemplary detector unit of the imaging device as shown in broken lines, the four energy sources and four detectors each being spatially positioned around a subject's body in an approximately diamond-shaped configuration, where the subject's body is oriented in an upright seated position in the scanner.
Figure 8:
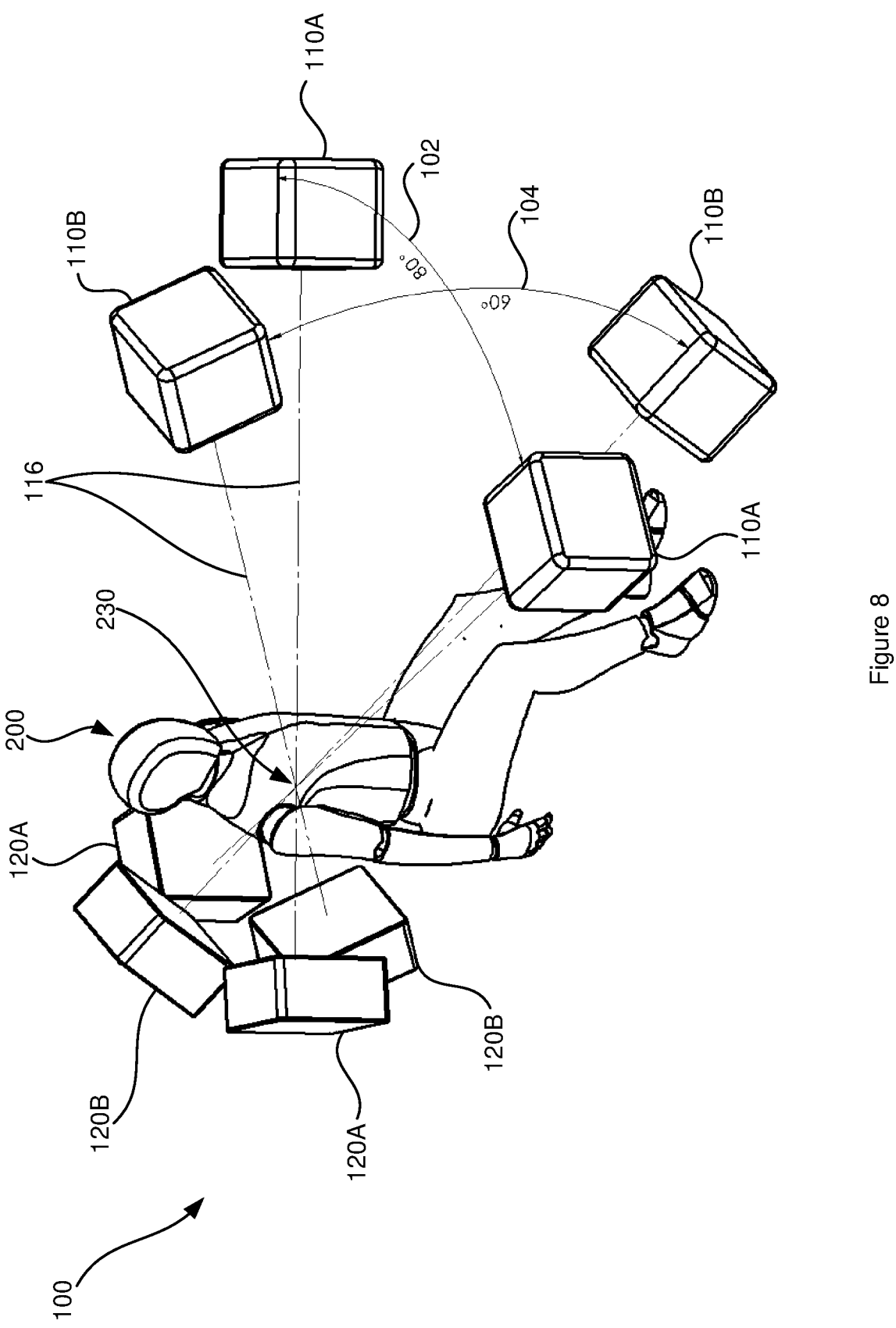
FIG. 8 is a perspective view of the imaging device of FIG. 7 excluding the exemplary detector unit and source unit for clarity.
Figure 9:
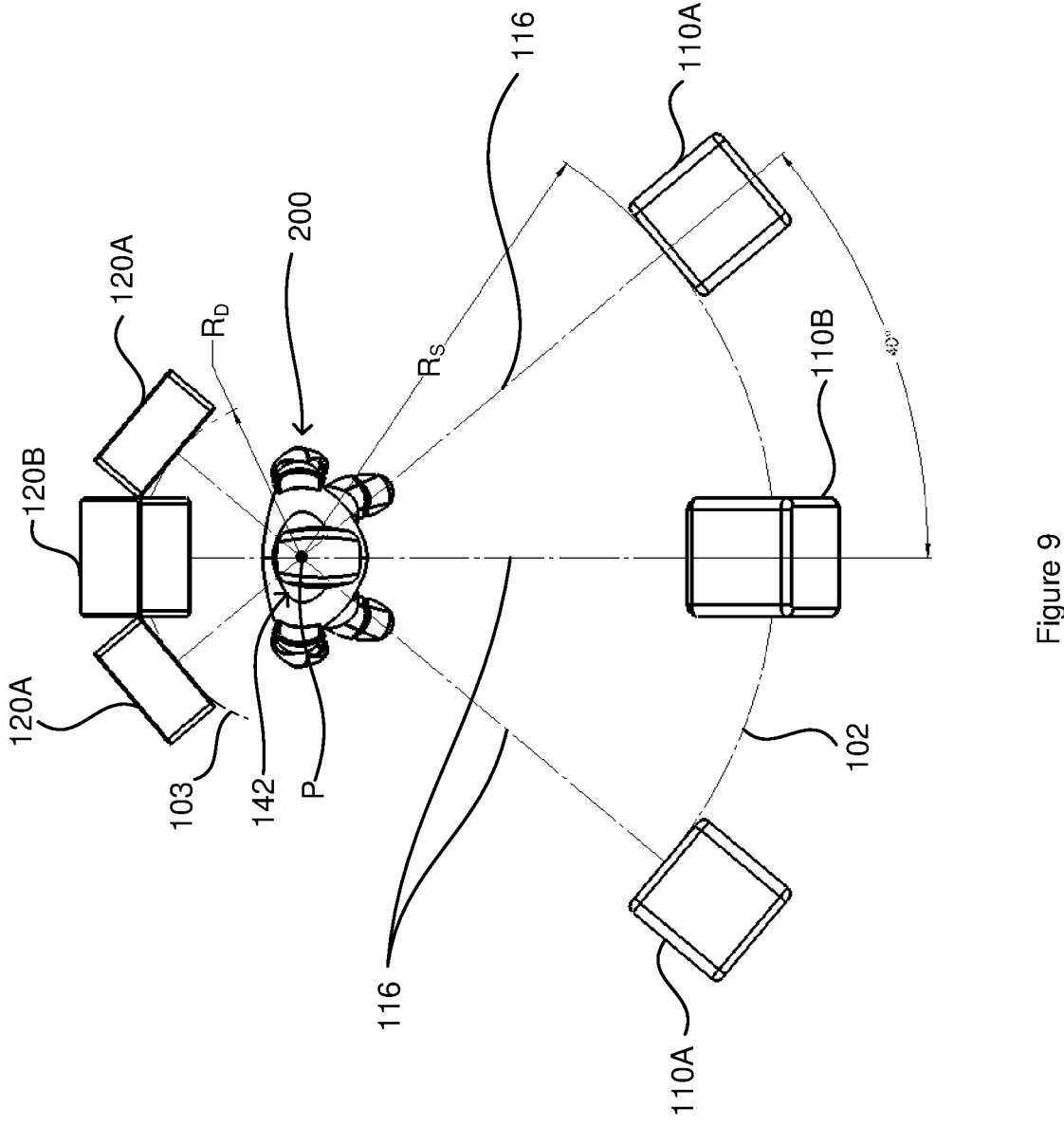
FIG. 9 is a plan view of the imaging device of FIG. 7 excluding the exemplary detector unit and source unit for clarity.

As shown in FIGS. 5 to 12, the pair of energy sources 110A may be provided on the first arc 102 and the pair of energy sources 110B may be provided on the second arc 104. However, the corresponding detectors pairs 120A, 120B may be provided on different common arcs from those of the first and second arcs 102, 104. This is best observed in the embodiments of FIG. 9 showing a plan view of the arrangement of the imaging device 100 of FIG. 7. The detector pairs 120A may be provided on a common arc 103 and the detector pairs 120B may be provided on another common arc (not shown). Where the energy sources 110A, 110B and detectors 120A, 120B are located on different common arcs, the length of the common arcs 102, 104 on which the energy sources are located preferably have a greater length than the common arcs (see arc 103 and other common arc not shown) on which the detectors are located. Thus, in the embodiments of FIGS. 5 to 12, the subject 200 may be located in closer proximity to the detectors 120A, 120B than the energy sources 110A, 110B within the imaging device 100. This will be described in more detail in relation to FIGS. 9 and 12.

Notably, the energy sources and detectors need not be provided on common arcs 102, 104 in the first and second planes and optionally, may not be aligned in the first and second planes around the subject's body 210, as would be appreciated by a person skilled in the art, and in view of the embodiments of the disclosure as described herein.

In the embodiment of FIG. 5, the two pairs of energy sources and detectors 110A, 120A in the first plane provide imaging angles that are circumferentially spaced apart at an angle of about 80 degrees. Furthermore, the two pairs of energy sources and detectors 110B, 120B in the second plane provide imaging angles that are circumferentially spaced apart at an angle of about 60 degrees as indicated.

FIG. 5 shows a diamond-shaped configuration of the energy sources 110A, 110B and the detectors 120A, 120B where the diamond is in the form of an addition or 'plus' sign centred relative to the region 230 of the subject's body 210 to be imaged at the intersection of the first and second planes. The imaging beams 116 generated by the energy sources 110A, 110B intersect through an intersection region 142, which may include a single intersection point P (see also FIGS. 9 and 12). The intersection region 142 of the imaging device 100 will correspond to the region 230 of the subject's body 210 to be imaged. The location of the intersection region 142 and intersection point P is dependent on the spatial arrangement of the energy sources 110A, 110B and detectors 120A, 120B, which can be selected based on a desired positioning of the subject 200 in the imaging device 100, as will be described in relation to FIGS. 9 and 12.

The first plane may be a horizontal or transverse plane and the second plane may be in a vertical or sagittal plane of the subject's body 210 as located in an upright standing position as shown in FIG. 5. The energy sources 110A may be circumferentially spaced about 40 degrees to the left or right of the intersection of the first arc 102 with the second arc 104. Furthermore, the energy sources 110B may be circumferentially spaced about 30 degrees above or below of the intersection of the second arc 104 with the first arc 102. Similar circumferential spacing may be provided with respect to the detectors 120A, 120B on their respective common arcs in the first and second planes (see e.g., common arc 103 for detectors 120A in FIGS. 9 and 12).

Although FIG. 5 depicts angles of about 60 and 80 degrees between the imaging angles or perspectives provided by the pairs of energy sources and detectors, embodiments of the disclosure are not limited to these angles, or to providing circumferential spacing on an arc in the planes. The imaging angles may be spaced further apart up to 180 degrees circumferentially around the subject's body 210. However, it is preferable that the energy sources 110A, 110B are closely positioned in order to provide a more compact scanner 100. Furthermore, the configuration of the energy sources 110A, 110B is also reflected in the corresponding arrangement of the detectors 120A, 120B as shown by the imaging beams 116 through the region 230. Thus, the detectors 120A, 120B are ideally closely positioned in order to provide a more compact scanner 100. This will be explained in more detail in relation to an exemplary source unit 112 and detector unit 122 as shown and described with respect to FIGS. 7, 10 and 13.

In some embodiments, the imaging angles provided by the pairs of energy sources and detectors 110A, 120A in the first plane may be spaced apart in a range of about 45 to 90 degrees, being preferably around 80 degrees apart in the diamond-shaped configuration as shown in FIG. 5. Although not shown, various other configurations of the energy sources and detectors may be provided such as a rectangular-shaped configuration, or an oval or elliptical-shaped configuration where additional energy sources and detectors are provided. Furthermore, irregular-shaped configurations may be provided.

In the diamond-shaped configuration of FIG. 5, the two imaging angles provided by the pairs of energy sources and detectors 110A, 120A may be spaced apart in the first plane in a range of about 45 to 70 degrees or about 70 to 90 degrees, or about 45 to 60 degrees, about 60 to 70 degrees, about 70 to 80 degrees or about 80 to 90 degrees. The spacing may be about 45 degrees, about 50 degrees, about 55 degrees, about 60 degrees, about 65 degrees, about 70 degrees, about 75 degrees, about 80 degrees, about 85 degrees or about 90 degrees. However, preferably the spacing is about 80 degrees as shown in FIG. 5 for the diamond-shaped configuration.

Furthermore, the two imaging angles provided by the pairs of energy sources and detectors 110B, 120B may be spaced apart in the second plane in a range of about 45 to 70 degrees. Preferably, the spacing is in a range of about 45 to 60 degrees or about 60 to 70 degrees. The spacing may be about 45 degrees, about 50 degrees, about 55 degrees, about 60 degrees, about 65 degrees or about 70 degrees. Preferably, the spacing is about 60 degrees as shown in FIG. 5 for the diamond-shaped configuration.

Figure 6:
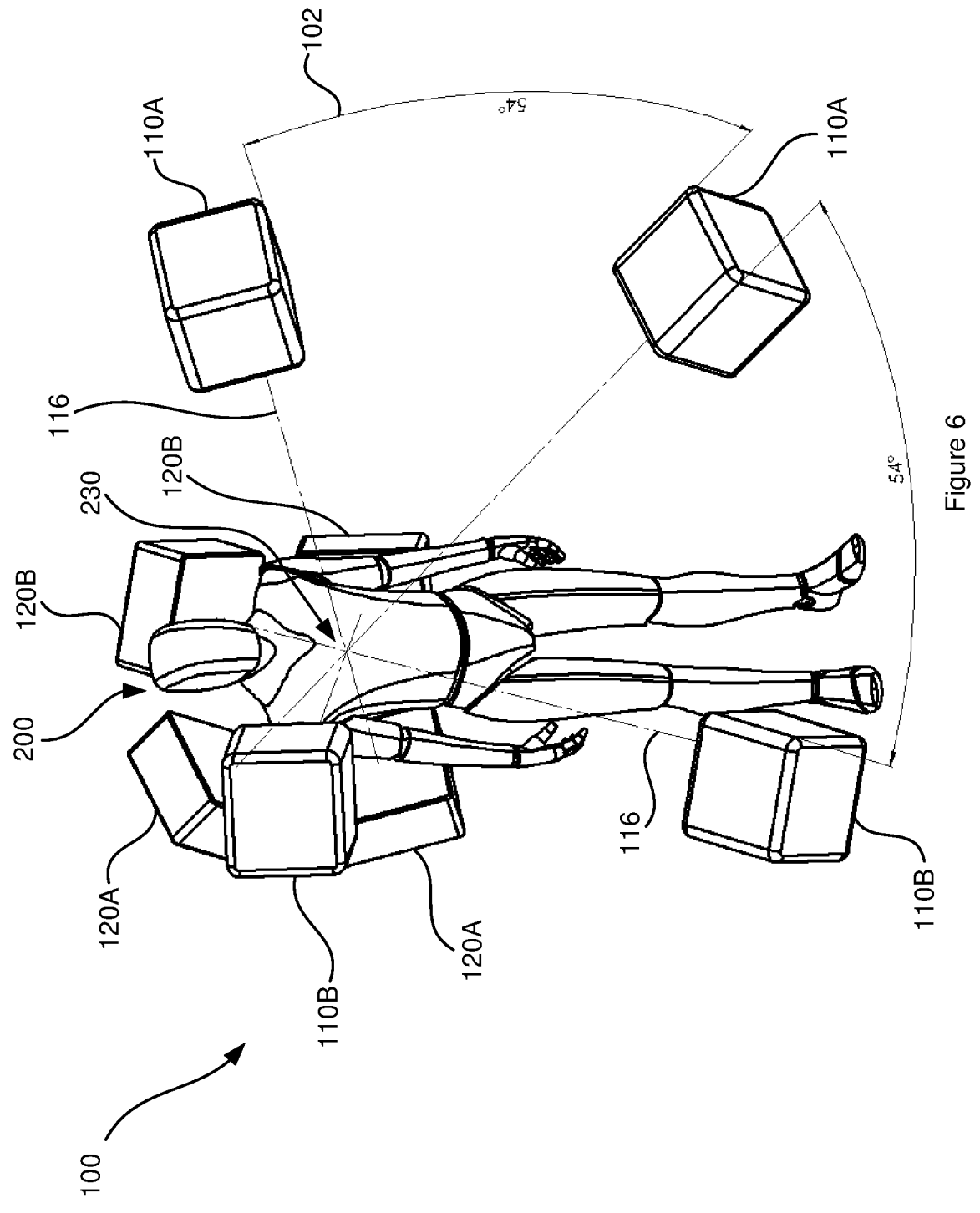
FIG. 6 is a perspective view of another imaging device according to some embodiments of the disclosure, showing four energy sources and four detectors each spatially positioned around a subject's body in an approximately square-shaped configuration, where the subject's body is oriented in an upright standing position in the scanner.

FIG. 6 is a perspective view of another imaging device 100 according to some embodiments of the disclosure, showing four energy sources 110 (denoted as 110A, 110B) and four detectors 120 (denoted as 120A, 120B) each spatially positioned around a subject's body 210 in a square-shaped configuration, where the subject's body 210 is oriented in an upright standing position in the scanner 100. Two pairs of energy sources and detectors 110A, 120A are spatially positioned around the subject's body 210 in a first plane and two pairs of energy sources and detectors 110B, 120B are spatially positioned around the subject's body 210 in a second plane. The first and second planes are angled relative to a sagittal or vertical plane of the subject's body 210. The second plane is offset at an angle of 54 degrees relative to the first plane, as indicated between the spacing of energy sources 110A and 110B near the subject's feet.

In relation to the square-shaped configuration of FIG. 6, four imaging angles may be provided by the pairs of energy sources and detectors 110A, 110B, and 120A, 120B which are spaced apart in the first and second planes in a range of about 45 to 70 degrees, being preferably around 54 degrees as shown. Preferably, the four imaging angles are spaced apart in a range of about 45 to 60 degrees or about 60 to 70 degrees. The spacing may be about 45 degrees, about 50 degrees, about 55 degrees, about 60 degrees, about 65 degrees or about 70 degrees. Preferably, the spacing is about 60 degrees, and more preferably about 54 degrees as shown in FIG. 6 in the square-shaped configuration.

Turning to FIGS. 7 to 9, another imaging device 100 is shown according to some embodiments of the disclosure, showing four energy sources 110 (denoted as 110A, 110B) positioned in an exemplary source unit 112 and four detectors 120 (denoted as 120A, 120B) positioned in an exemplary detector unit 122 of the imaging device 100. The source unit 112 and detector unit 122 are shown in broken lines indicating that this is only an exemplary embodiment of the shape and location of these units in the scanner 100. The four energy sources 110 and four detectors 120 are each spatially positioned around the subject's body 210 in a diamond-shaped configuration as described in relation to the embodiment of FIG. 5. However, the subject's body 210 is now oriented in an upright seated position in the scanner 100 which includes a seat or chair 124 as part of the detector unit 122. FIG. 8 shows the same imaging device 100 of FIG. 7 although excludes the source unit 112 and detector unit 122 for clarity. The imaging angles and/or angles between the energy sources 110 and/or detectors 120 may be substantially similar to those of the diamond-shaped configuration described in relation to the embodiment of FIG. 5.

As can be observed in FIG. 7, the imaging device 100 is configured to accommodate the subject 200 in an upright orientation between the energy sources 110 and detectors 120. The subject 200 may be positioned on a seat 124 of the detector unit 122 for image acquisition. In alternative embodiments, the seat 124 may be excluded and able-bodied subjects 200 may be able to walk into the scanner 100 and position themselves in a standing position between the source unit 112 and detector unit 122 for image acquisition. In some embodiments, the energy sources 110 are spaced approximately 1200 mm relative to the patient's spine, while the detectors 120 are spaced approximately 400 mm relative to the patient's spine. This provides a sufficient gap of at least 1000 mm between the source unit 112 and detector unit 122 for the subject 200 to walk into and/or be positioned in the scanner 100.

FIG. 9 shows the imaging device 100 of FIG. 7 in a plan view excluding the source unit 112 and detector unit 122 for clarity. FIG. 9 illustrates that the imaging beams 116 generated by the energy sources 110A, 110B intersect through an intersection region 142, which may include a single intersection point P. The intersection region 142 of the imaging device 100 will correspond to the region 230 of the subject's body 210 to be imaged. The intersection point P is not equidistant from each of the energy sources 110A, 110B and detectors 120A, 120B. In the embodiments of FIGS. 5 to 12, the intersection point P is located closer to the detectors 120A, 120B than the energy sources 110A, 110B (in comparison to FIGS. 3 and 4 in which the intersection point P would be equidistant from the energy sources and detectors). A radius of curvature from the intersection point P to the common arc 103 on which the pair of detectors 120A are located, denoted as $R_D$, may be about 400 mm, or more particularly, about 410 mm. A radius of curvature from the intersection point P to the first arc 102 on which the pair of sources 110A are located, denoted as $R_S$, may be about 1200 mm.

The advantage of having the intersection region 142 and more particularly, the intersection point P, being closer to the detectors 120A, 120B than the energy sources 110A, 110B, is that this reduces the magnification of the images acquired by the imaging device 100. Magnification occurs when the energy sources 110A, 110B are positioned too close to the region being imaged, e.g., the region 230 of the subject 200, and the image captured exaggerates the size and dimensions of the structures. In embodiments of the disclosure, it may be desirable to reduce the magnification in order to provide a more accurate representation of the region 230 to be imaged. A posterior-anterior (PA) projection beam view allows a more accurate representation of the region 230 to be imaged, such as particularly the heart or lungs of the subject

200, as the region 230 is positioned in closer proximity to the detectors 120A, 120B and is therefore less magnified. A person skilled in the art would appreciate that the radii of curvature $R_S$ and $R_D$ may be varied as appropriate for the dimensions of the imaging device 100, although it remains preferable that the radius $R_S$ is greater than the radius $R_D$.

FIGS. 10 to 12 show another imaging device 100 according to some embodiments of the disclosure, having a similar arrangement to FIGS. 7 to 9, except that the two detectors 120B are angled relative to the respective energy sources 110B. The two detectors 120B indirectly face the respective energy sources 110B and are angled such that the imaging beams 116 generated by the energy sources 110B are not substantially orthogonal with the detectors 120B. While the two detectors 120B are angled towards the respective energy sources 110B, similar to the detectors 120A and respective energy sources 110A, the two detectors 120B are co-planar and vertically oriented relative to one another. More specifically, the two detectors 120B are positioned one above the other in the imaging device 100.

The detectors 120B are not provided on a common arc in a plane through the subject's body 210. In contrast, the energy sources 110A are provided on a first arc 102 in a first plane through the subject's body 210, the energy sources 110B are provided on a second arc 104 in a second plane through the subject's body 210, and the detectors 120A are provided on a different arc 103 in the second plane through the subject's body 210 as shown in FIG. 12. While the two pairs of energy sources and detectors 110A, 120A are provided in the first plane and two pairs of energy sources and detectors 110B, 120B are provided in the second plane, the detectors 120B are not provided on a common arc in the second plane.

The advantage of the alternative arrangement of FIGS. 10 to 12 is that the two co-planar detectors 120B enable the imaging device 100 to be more compact. The detector unit 122 can thus be narrower as the vertically-oriented detectors 120B, which are not located on a common arc, have less width than in the arrangement of FIGS. 7 to 9. Thus, an even smaller, more compact imaging device may be provided by this inventive embodiment that still allows for multiple images to be acquired at different angles through the subject's body 210. In other embodiments (not shown), the two detectors 120A may be angled relative to the respective energy sources 110A. The two detectors 120A may indirectly face the respective energy sources 110A and be angled such that the imaging beams 116 generated by the energy sources 110A are not substantially orthogonal with the detectors 120A. The two detectors 120A may be co-planar and horizontally oriented relative to one another. In some embodiments (not shown), all of the detectors 120A, 120B may be co-planar relative to one another while remaining angled towards the respective energy sources 110A, 110B to acquire the images. This may advantageously further reduce the width of the detector unit 122, thereby providing a more compact and smaller imaging device 100.

Advantageously, the configuration of the energy sources 110 and detectors 120 in the inventive imaging device 100 may enable a compact device to be manufactured that provides for multiple images to be acquired simultaneously or at substantially the same time without the need for moving parts during acquisition (such as a C-arm or ring in typical CT scanners). The energy sources 110 and detectors 120 are stationary during scanning and fixed in position in the imaging device 100 in contrast to typical CT scanners. The configuration of the energy sources 110 and detectors 120 can also provide close positioning of the components through the various arrangements described herein to allow for more efficient use of the three-dimensional space within the scanner body as the energy sources 110 and detectors 120 can take up less overall space in contrast to e.g., the system 10 of FIGS. 1 and 2.

Figure 13:
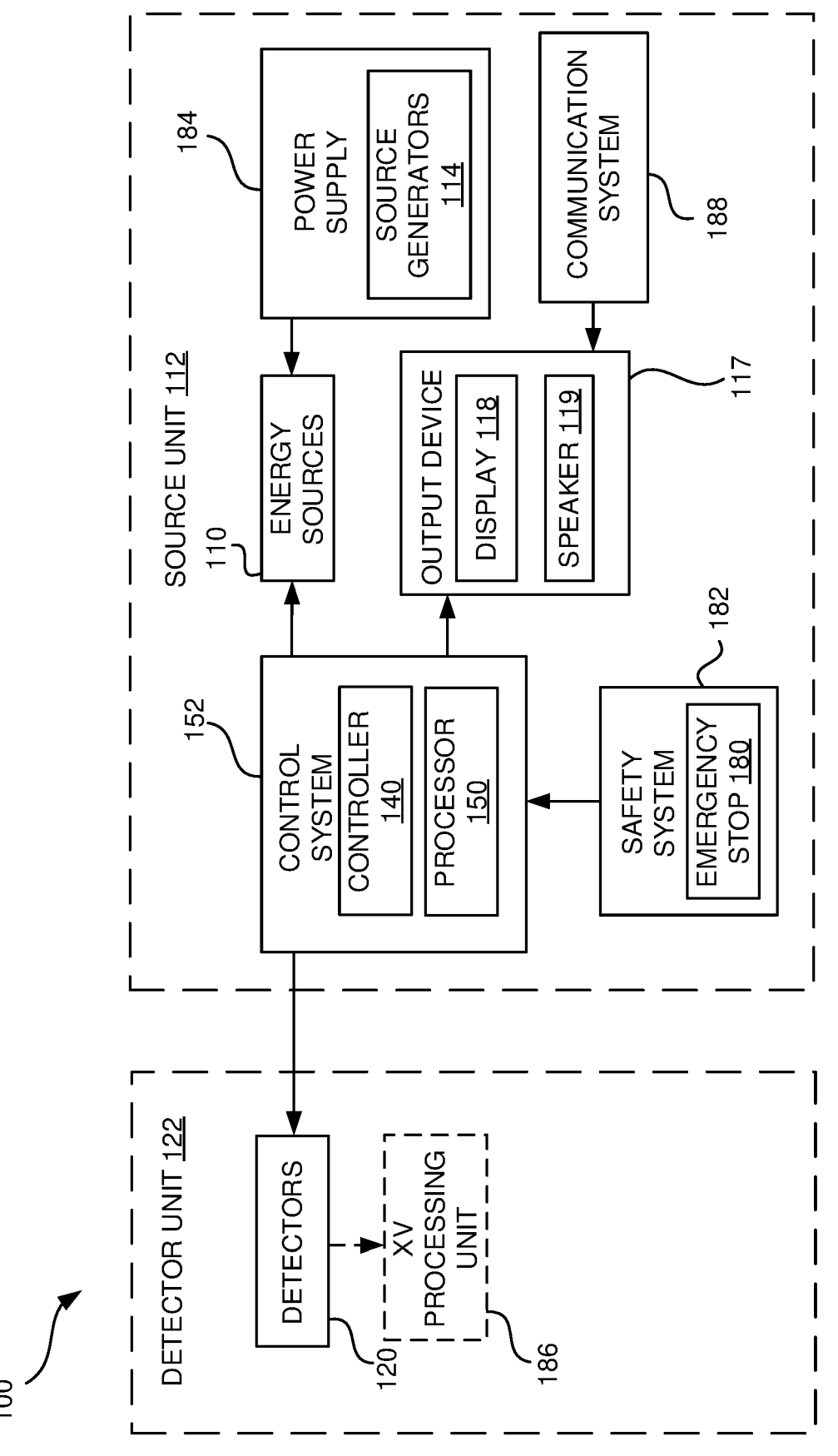
FIG. 13 is a schematic diagram showing components of an exemplary detector unit and source unit of the imaging device of FIGS. 7 to 12 according to some embodiments of the disclosure.

In the embodiments described herein, all of the sources 110 may be located on one side of the imaging device 100, such as in front of the subject's body 210, and all of the detectors 120 may be located on an opposite side of the imaging device 100, such as behind the subject's body 210, which is shown in FIGS. 7 to 12. The sources 110 may all be located within a first housing denoted as the source unit 112 and the detectors 120 may all be located within a second housing denoted as the detector unit 122 as shown in FIGS. 7, 10 and 13. Thus, there is greater space between the source unit 112 and detector unit 122 for the subject 200 to move in and out of the scanner 100 as the sources 110 and detectors 120 may extend circumferentially around the subject 200 at angles of substantially less than 180 degrees, such as only approximately 45 to 90 degrees to provide the imaging angle in the first plane (see FIGS. 5 to 12).

Therefore, not only does the inventive imaging device 100 provide a more compact scanner without moving parts for acquisition, it also enables the subject 200 to be readily positioned within the scanner, such as by walking between the source unit 112 and detector unit 122 and being positioned in an upright seated or standing position in the scanner. This advantageously enables access to the imaging device 100 for various patient groups, including young children, the elderly, and patients with language, hearing or cognitive impairment, who are unable to be readily scanned due to positioning issues within traditional scanners and/or the inability to follow instructions for the scanning to be completed.

In relation to dynamic in vivo imaging of the lungs, the images of the most value include those where the individual lungs are separated on the images and there is minimal bone obstruction. Thus, the most valuable angle to image is in the sagittal or vertical plane through the subject's body as the lungs are separated by the spinal column. As the imaging angle increases relative to the spinal axis of the patient, the lungs start to overlap from about 40 degrees and with further angle increase, the spine and arms of the patient may also be included in the image. Thus, there is a necessary balance of having sufficient views or perspectives of images at suitable separation in order to reconstruct those images to show dynamic lung function. The inventors have found that the energy sources and detectors in the scanner can be positioned closely together, by providing at least one energy source and at least one detector on a different plane to the remaining energy sources and detectors. This enables sufficient perspectives of images to be acquired for dynamic in vivo imaging, while advantageously reducing the space required.

FIG. 13 shows a schematic diagram of components of an exemplary source unit 112 and detector unit 122 of the imaging device 100 according to some embodiments of the disclosure. The detector unit 122 and source unit 112 are shown in broken lines to indicate that this is an exemplary arrangement of the components and systems of the imaging device 100, which may vary as would be understood by the skilled addressee. For example, the XV processing unit 186 (optionally provided in the detector unit 122) may instead be located in the source unit 112. Alternatively, the XV processing unit 186 may not be included in the imaging device 100 and may instead be provided via a cloud-based server having the XV processing application for off-board processing of the image data. Moreover, in some embodiments, the control system 152, the safety system 182, the output device 117 and the communication system 188 of the source unit 112 may instead be located in the detector unit 122.

The processor 150 and processing unit 186 of FIG. 13 used to implement certain steps of the method 300 of embodiments of the disclosure (see FIG. 14) and performed in the functioning of the imaging device 100 may include a micro-processor configured to receive data from components of the device 100 or a computing server, such as through a wireless or hard-wired connection (not shown). The controller 140 may include a programmable logic controller (PLC) and/or an embedded PCB (not shown). The controller 140 may contain or store a number of predefined protocols or steps in a non-volatile memory such as a hard drive. Protocols may be programmable by the operator of the imaging device 100 to implement a number of steps for the method 300 as performed by the processors 150 and 186, or they may be predefined. Additionally/alternatively, the controller 140 and processors 150 and 186 may include any other suitable processor or controller device known to a person skilled in the art. The steps performed by the processors 150 and 186 may be implemented through a controller 140 and further in software, firmware and/or hardware in a variety of manners as would be understood by a person skilled in the art.

FIG. 13 also excludes some additional components and systems which would form part of the imaging device 100 to simplify the diagram. For example, the imaging device 100 may include one or more memory devices (not shown) in order to store various types of data including image data and prior-acquired patient data, and also software instructions for performing image acquisition processing workflows and XV processing, as will be described in more detail. The schematic diagram of FIG. 13 also omits some of the internal bus lines between various components and systems for simplicity. The excluded aspects would be readily appreciated by a person skilled in the art who would be able to readily supply the omitted software, firmware and/or hardware.

The source unit 112 includes one or more energy sources 110 (ideally at least three energy sources denoted as 110A, 110B) which are powered by one or more source generators 114 forming part of a power supply 184 for the imaging device 100. A control system 152 having the controller 140 and processor 150 may be configured to operate the energy sources 110 and detectors 120 of the detector unit 122 for scanning the region 230 of the subject's body 210. The source unit 112 may also include a safety system 182 in communication with the control system 152. The safety system 182 may include an emergency stop 180 in the form of a software or hardware component of the imaging device 100. The emergency stop 180 may be located on a surface of the source unit 112 adjacent the subject 200 (not shown). The emergency stop 180 may include an actuator, such as a depressible button or switch, for powering off the imaging device 100 in the event of an emergency. If the emergency stop 180 is actuated, the controller 140 of control system 152 may be operable to stop acquisition of the images via the energy sources 110 and optionally, directly switching off power to the imaging device 100 via the power supply 184 (not shown), in order to prevent inadvertent generation of radiation or energy.

The source unit 112 may also include an output device 117 which may include a display 118 and a speaker 119 as shown in FIG. 13. A display 118 may be located on a surface of the source unit 112 (not shown) in the subject's line of sight when positioned in the scanner 100. Although not shown, the imaging device 100 may also include a speaker 119 positioned in the source unit 112 and/or the detector 122. The output device 117 is provided to enable communications to be delivered to and/or from the subject 200 and/or operator and the imaging device 100 via a communication system 188. For example, the control system 152 via the processor 150 may output instructions to the subject 200 and/or operator via the output device 117. The instructions may be provided on the display 118 and/or via the speaker 119.

As shown in FIG. 13, the detector unit 122 includes one or more detectors 120 (preferably at least three detectors 120A, 120B) operable by the controller 140 of the control system 152 for acquiring a time series of in vivo images of the region 230 of the subject's body 210. The images acquired may be used as an input to the XV processing unit 186, as previously described, for producing XV three-dimensional motion fields of the region 230 of the subject's body 210, such as the lungs or heart. The XV processing unit 186 may alternatively be provided off-board via a server or cloud-based system in some embodiments.

FIG. 14 illustrates a method 300 for acquiring a time series of in vivo images of a region 230 of a subject's body 210 according to some embodiments of the disclosure. The method 300 includes a step 302 of providing an imaging device 100 including at least three energy sources 110 (denoted as 110A, 110B) and at least three detectors 120 (denoted as 120A, 120B) for detecting energy from the at least three energy sources 110 passing through the region 230 of the subject's body 210 located between the energy sources 110 and the detectors 120. The imaging device 100 also includes a controller 140 configured to operate the at least three energy sources 110 and the at least three detectors 120 to acquire a time series of in vivo images of the region 230 of the subject's body 210. The method also includes a step 306 of operating the controller 140 to acquire the time series of in vivo images of the region 230 of the subject's body 210.

The imaging device 100 may include one or more features as described herein and in relation to the embodiments of FIGS. 3 to 13. The imaging device 100 includes at least two pairs of energy sources and detectors 110A, 120A spatially positioned around the subject's body 210 in a first plane, and at least one pair of energy sources and detectors 110B, 120B spatially positioned around the subject's body in a second plane. The first plane and the second plane intersect through the region 230 of the subject's body to be imaged.

As shown in FIG. 14, the method 300 optionally includes the step 304, performed before operating the controller 140 to acquire the images, of positioning the subject 200 in the imaging device 100 in an upright orientation between the energy sources 110 and detectors 120. For example, the subject 200 may be positioned in an upright standing position as shown in the embodiments of the imaging device 100 of FIGS. 5 and 6. Alternatively, the subject 200 may be positioned in an upright seated position in the imaging device 100 as shown in the embodiments of FIGS. 7 to 12. For able-bodied patients 200, they may simply walk into the space between the energy sources 110 and detectors 120 and sit down on the seat 124 or alternatively, position themselves in a standing or upright position for the image acquisition. For wheelchair or limited mobility patients, an operator may assist with transfer to the seat 124 or a wheelchair with radiolucent seat back may be provided and positioned in the scanner 100. After this step is complete, either the operator or the communication system 188 may advise the subject 200 of the estimated duration of the scan.

In some embodiments, the method 300 may also include two optional steps 308 and 310 as shown in broken lines in FIG. 14. The method 300 may include the step 308 of operating the controller 140 to acquire a time series of in vivo images of the region 230 of the subject's body 210 simultaneously or at substantially the same time from each of the detectors 120. The controller 140 is configured to acquire at least three time series of in vivo images of the region 230 of the subject's body 210. However, in some embodiments where the imaging device 100 includes four energy sources 110 and four detectors 120, the controller is configured to acquire four time series of in vivo images of the region 230 of the subject's body 210.

Multiple time series of images may be advantageously acquired by the imaging device 100 and method 300 simultaneously or at substantially the same time over part of the breath or over a full breath of the subject 200. Preferably, the time series of images are acquired over a full single breath of the subject 200. Acquiring multiple time series (from different angles) of a single breath, rather than acquiring a single time series (from different angles) of multiple breaths, removes the requirement for the subject 200 to maintain consistent breathing across multiple breaths. The controller 140 may operate each energy source 110 and corresponding detector 120 to acquire the images at the same or substantially the same time. Instead of operating the energy sources 110 and corresponding detectors 120 simultaneously, it may be preferable to sequentially acquire the images with a short timing offset for operation of the energy source/detector pairs. This may advantageously reduce x-ray backscatter and thus improve the image quality. The processor 140 may be configured to correct for the timing differences between the time series of images acquired when processing the data. Advantageously, for imaging devices 100 employing the use of x-rays, this reduces the radiation dosage as all of the energy sources 110 and corresponding detectors 120 may be simultaneously or at substantially the same time operated by the controller 140 for a short time to acquire the images.

By taking images simultaneously or at substantially the same time and of a single breath, the inventive device 100 reduces the radiation dosage and scanning duration as fewer separate images need to be taken and all images are acquired typically within one breath, taking around four seconds. In comparison, legacy hardware such as fluoroscopes requires repositioning of the system for each image, and scanning four separate breaths, resulting in a scan that takes a considerable amount of time and contains inaccuracies due to measurements being acquired over four different breaths. Acquiring a full single breath simultaneously or at substantially the same time, rather than four separate breaths, advantageously allows for use of the imaging device 100 by younger patients, such as children older than three years, and also elderly patients, by reducing the radiation dosage, shortening the scanning time, and removing the requirement for the patient 200 to maintain consistent breathing across multiple breaths.

Once the scan has finished after step 308, the image data may be uploaded to the XV processing unit 186, which is located either on-board the imaging device 100 or accessed via a cloud-based server and XV processing application. This step 310 may be initiated upon action taken by the operator or the processor 150 may be configured to automatically upload the image data once the scanning is complete. As shown in FIG. 14, the method 300 may also include the step 310 of using a processor 150, 186 (see FIG. 13) or off-board XV processing application to reconstruct a three-dimensional motion field of the region 230 of the subject's body 210 based on the time series of images acquired from the detectors 120 in step 308. This may employ XV processing techniques described in previously mentioned International Patent Publication Nos. WO 2011/032210 A1 and WO 2015/157799 A1 and incorporated herein by reference. The processor 150 may produce three-dimensional (i.e., three spatial dimensions) motion measurements (e.g., displacement or velocity measurements) over the time of the region 230 that was imaged (which would result in four-dimensional measurements, i.e., three spatial dimensions plus time). In addition, the three-dimensional motion measurements may have either one component of velocity (3D1C), two components of velocity (3D2C), or preferably three components of velocity (3D3C). Advantageously, there is no need for the energy sources 110 and detectors 120 to rotate around the subject's body 210 to acquire a number of images from different angles as per existing CT scanners. Beneficially, the energy sources 110 and detectors 120 remain stationary throughout the imaging process and a sufficient number of angles or perspective of images may be acquired through the inventive arrangement of the energy sources 110 and detectors 120 as described herein. This further reduces the x-ray radiation dosage for imaging devices 100 employing x-rays as fewer separate images need to be taken and a shorter scanning duration is required.

Embodiments of the disclosure may advantageously provide an imaging device 100 and an imaging method 300 which utilises an inventive configuration of energy sources and detectors for acquiring multiple images simultaneously or at substantially the same time (potentially with a short timing offset) without the need for moving parts during acquisition, such as a ring or C-arm of existing CT scanners. The inventive configuration may enable a compact imaging device 100 to be provided as the energy sources and detectors can be located closely together instead of being spaced at least 180 degrees around the subject's body 210 or entirely 360 degrees in rotation in contrast to the system 10 of FIGS. 1 and 2, thereby reducing the size of the source and detector units. By taking images simultaneously or at substantially the same time, embodiments of the inventive device 100 and method 300 of imaging may reduce the radiation dosage as fewer separate images need to be taken and a shorter scanning duration is required. Furthermore, quality of the images is not compromised as the imaging device 100 and method 300 of imaging may still acquire images suitable for use with XV technology and for generating three-dimensional motion fields of the region 230 imaged.

Embodiments of the imaging device 100 and method 300 of imaging may advantageously be used by younger patients, such as older than three years, through reducing the radiation dosage and shortening the scanning time. Embodiments of the inventive imaging device 100 and method 300 of imaging may also encourage use by young children, the elderly and mobility-impaired patients by providing a walk-in scanner which allows for scanning of the patient 200 in a seated or upright standing position. By enabling positioning of the patient 200 in the scanner 100 in an anatomically favourable orientation for scanning, namely being upright in a seated or standing position, the patient 200 is also able to breathe normally during image acquisition to improve the imaging quality and assessment of organ structure and function, particularly the lungs of the subject 200.

It is to be understood that various modifications, additions and/or alternatives may be made to the parts previously described without departing from the ambit of the present disclosure as defined in the claims appended hereto.

Where any or all of the terms "comprise", "comprises", "comprised" or "comprising" are used in this specification (including the claims) they are to be interpreted as specifying the presence of the stated features, integers, steps or components, but not precluding the presence of one or more other features, integers, steps or components or group thereof.

It is to be understood that the following claims are provided by way of example only, and are not intended to limit the scope of what may be claimed in any future application. Features may be added to or omitted from the claims at a later date so as to further define or re-define the disclosure.

The invention claimed is:

1. An imaging device for acquiring a time series of dynamic in vivo images of a region of a subject's body, the imaging device comprising:
   at least three energy sources;
   at least three detectors for detecting energy from the at least three energy sources passing through the region of the subject's body located between the energy sources and detectors, wherein at least two pairs of energy sources and detectors are spatially positioned around the subject's body in a first plane, and at least one pair of energy sources and detectors is spatially positioned around the subject's body in a second plane, wherein the first plane and the second plane intersect through the region of the subject's body to be imaged; and
   a controller configured to operate the energy sources and detectors to acquire at least three time series of dynamic in vivo images of the region of the subject's body.

2. The imaging device according to claim 1, wherein the controller is configured to acquire the images using at least three imaging angles through the region of the subject's body, wherein at least two imaging angles are provided in the first plane through the subject's body, and at least one imaging angle is provided in the second plane through the subject's body.

3. The imaging device according to claim 2, wherein the at least two imaging angles in the first plane are spaced apart in a range of about 45 to 90 degrees.

4. The imaging device according to claim 1, wherein at least one of the detectors is angled relative to the respective energy source.

5. The imaging device according to claim 1, wherein the at least two energy sources and the at least two detectors in the first plane are each located on a respective common arc in the first plane through the subject's body.

6. The imaging device according to claim 1, further comprising at least four energy sources and at least four detectors, wherein at least three pairs of energy sources and detectors are spatially positioned in the first plane, and at least one pair of energy sources and detectors is spatially positioned in the second plane.

7. The imaging device according to claim 6, wherein the controller is configured to acquire the images using at least four imaging angles through the region of the subject's body, wherein at least three imaging angles are provided in the first plane through the subject's body, and at least one imaging angle is provided in the second plane through the subject's body.

8. The imaging device according to claim 6, wherein the at least three energy sources and the at least three detectors in the first plane are each located on a respective common arc in the first plane through the subject's body.

9. The imaging device according to claim 1, wherein at least one pair of energy sources and detectors is located in both of the first and second planes.

10. The imaging device according to claim 1, further comprising at least four energy sources and at least four detectors, wherein at least two pairs of energy sources and detectors are spatially positioned in the first plane and at least two pairs of energy sources and detectors are spatially positioned in the second plane.

11. The imaging device according to claim 10, wherein the controller is configured to acquire the images using at least four imaging angles through the region of the subject's body, wherein at least two imaging angles are provided in the first plane through the subject's body, and at least two imaging angles are provided in the second plane through the subject's body.

12. The imaging device according to claim 10, wherein at least two of the detectors are angled relative to the respective energy sources, and at least two of the detectors are substantially aligned with the respective energy sources.

13. The imaging device according to claim 10, wherein the at least two energy sources and the at least two detectors in the second plane are each located on a respective common arc in the second plane.

14. The imaging device according to claim 1, wherein the second plane is offset at an angle of about 70 to 90 degrees relative to the first plane.

15. The imaging device according to claim 1, wherein the device is configured to accommodate the subject in an upright orientation between the energy sources and detectors.

16. The imaging device according to claim 1, wherein the device is configured to accommodate the subject between the energy sources and detectors in a position that is closer to the detectors than the energy sources.

17. The imaging device according to claim 1, wherein the controller is configured to operate the energy sources and detectors to acquire a time series of in vivo images of the region of the subject's body simultaneously or at substantially the same time from each of the detectors.

18. The imaging device according to claim 17, further comprising a processor configured to reconstruct a three-dimensional motion field based on the time series of images acquired from each of the detectors.

19. The imaging device according to claim 1, wherein the at least three time series of dynamic in vivo images of the region of the subject are acquired while the energy sources and detectors remain stationary.

20. The imaging device according to claim 1, wherein the region of the subject's body to be imaged includes at least part of the lungs of the subject and the time series of images are acquired while the subject is breathing.

21. A method for acquiring a time series of dynamic in vivo images of a region of a subject's body, the method comprising the steps of:
   providing an imaging device including:
      at least three energy sources;
      at least three detectors for detecting energy from the at least three energy sources passing through the region of the subject's body located between the energy sources and detectors, wherein at least two pairs of energy sources and detectors are spatially positioned around the subject's body in a first plane, and at least one pair of energy sources and detectors is spatially positioned around the subject's body in a second plane, wherein the first plane and the second plane intersect through the region of the subject's body to be imaged; and
      a controller configured to operate the energy sources and the detectors to acquire at least three time series of dynamic in vivo images of the region of the subject's body; and
   operating the controller to acquire the time series of dynamic in vivo images of the region of the subject's body.

22. The method according to claim 21, further comprising the step of: operating the controller to acquire a time series of in vivo images of the region of the subject's body simultaneously or at substantially the same time from each of the detectors.

23. The method according to claim 22, further comprising the step of:
   reconstructing, using a processor, a three-dimensional motion field based on the time series of images acquired from each of the detectors.

24. The method according to claim 21, wherein the at least three time series of dynamic in vivo images of the region of the subject are acquired while the energy sources and detectors remain stationary.

* * * * *